United States Patent [19]

Hershberger et al.

[11] Patent Number: 4,506,013
[45] Date of Patent: Mar. 19, 1985

[54] STABILIZING AND SELECTING RECOMBINANT DNA HOST CELLS

[75] Inventors: Charles L. Hershberger, New Palestine; Anna K. Radue, Martinsville; Paul R. Rosteck, Jr., Beech Grove, all of Ind.

[73] Assignee: Eli Lilly and Company, Indianapolis, Ind.

[21] Appl. No.: 275,088

[22] Filed: Jun. 18, 1981

Related U.S. Application Data

[63] Continuation-in-part of Ser. No. 193,556, Oct. 3, 1980, abandoned.

[51] Int. Cl.$^3$ .............. C12N 15/00; C12N 1/20; C12N 1/06; C12N 1/00; C12P 21/00; C12P 21/02; C12P 19/34; C12R 1/19
[52] U.S. Cl. .............. 435/172.3; 435/253; 435/259; 435/317; 435/68; 435/70; 435/91; 435/849; 435/29; 435/72; 435/73; 435/83
[58] Field of Search .............. 435/172, 317, 253, 68, 435/70, 172.3, 259

[56] References Cited

U.S. PATENT DOCUMENTS 4,356,270 10/1982 Itakura .............. 435/317
4,366,246 12/1982 Riggs .............. 435/68

FOREIGN PATENT DOCUMENTS 9930 4/1980 European Pat. Off.
19877 10/1980 European Pat. Off.
2007676A 5/1979 United Kingdom.

OTHER PUBLICATIONS

Lewin; Gene Expression-3, John Wiley & Sons, New York, 1977, pp. 352-380.
Honigman et al.; Gene 13, 289-298, (1981).
ATCC Catalog, Fifteenth edition, 1982, pp. 259 and 730.
Westoo et al.: Molec. gen. Genet. 178, 101, (1980).
Hayes: The Genetics of Bacteria and Their Viruses, Second Edition, J. Wiley & Sons, New York, 1968, p. 193.
Bolivar, F. et al., 1979, Life Sci. 25:807-818.
Goeddel, D. V., 1979, Nature 281:544-548.
Goeddel, D. V. et al., 1979, Proc. Nat'l. Acad. Sci. USA 76(1): 106-110.
Itakura, K. et al., 1977 Science 198:1056-1063.
West, R. W., 1979, Gene 7:271-288.
Rodriguez, R. L. et al., 1979, Nucleic Acids Research 6(10): 3267-3287.
Appleyard, R. K., 1954, Genetics 39:440-452.
Bachmann, B. J., 1972, Bacteriological Review 36(4):525-555.
Mauer, R., 1980, Mol. Biol. 139:147-161.
Kaiser, A. D., 1957, Virology 3:42-61.
Berg, D. E., 1974, Virology 62:224-233.
Schumann, W., 1979, Molec. Gen. Genet. 174:221.
Science 196 (4286): 182—183 (1977), Backman et al.
Cell 20: 529-542 (1980), Meacock and Cohen.
Proceedings of the National Academy of Science (USA), 73(11): 4174-4178 (1976), Backman et al.
Febs Letters 87(2): 277-282 (1978), Fernandez et al.
Journal of General Microbiology 118: 253-261, (1980), Imanaka et al.
Gene 1: 141-152 (1977), Nagahari et al.
Journal of General Molecular Genetics 178: 101-109, (1980), Westöö and Ljungquist.
Journal of General and Molecular Genetics 180: 147 (1980), Melechen et al.
Bolivar et al., Gene 2:75 (1977).
Crea et al., PNAS 75:5765 (1978).

(List continued on next page.)

Primary Examiner—Alvin E. Tanenholtz
Assistant Examiner—James Martinell
Attorney, Agent, or Firm—Gerald V. Dahling; Arthur R. Whale

[57] ABSTRACT

A method for stabilizing and selecting host cells containing recombinant DNA which expresses a functional polypeptide and the novel organisms and cloning vectors for the practice thereof. The invention further provides a simple, convenient, and inexpensive method to lyse host cells for purification of intracellular products.

134 Claims, 9 Drawing Figures

OTHER PUBLICATIONS

Bertani and Bertani, *J. Gen. Virol.* 6:201 (1970).

Stanier et al., 1976, The Microbial World, Prentice-Hall, Inc., Englewood Cliffs, New Jersey, pp. 382–386.

Hayes, W. H., 1968, The Genetics of Bacteria and their Viruses, John Wiley & Sons, Inc., New York, p. 411.

Campbell, A. M., 1969, Episomes, Harper & Row, New York, p. 18.

Miller, J. H., 1972, Experiments in Molecular Genetics, Cold Spring Harbor Laboratory, Cold Spring Harbor, New York, pp. 13 (Strain List), 41, 202, 203, 238, 239, 271–277 and 331–335.

Davis et al. 1980, Advanced Bacterial Genetics, CSH, New York, pp. 1, 7, 9, 49 and 240.

Letter from Mrs. Bobbie A. Brandon, American Type Culture Collection, 1-26-83, Rockville, Maryland, 20852.

Restriction Site and Functional Map of Plasmid pIA2

(11.0 kb) Arrows Indicate Direction of Transcription

Restriction Site and Functional Map of Plasmid pAR2

(13.4kb) Arrows Indicate Direction of Transcription

Restriction Site and Functional Map of Plasmid pIA7Δ4Δ1
(5270 bp) Arrows Indicate Direction of Transcription

Restriction Site and Functional Map of Plasmid pPR1

(7710 bp) Arrows Indicate Direction of Transcription

Restriction Site and Functional Map of Plasmid pIB7△I△4
(5295 bp) Arrows Indicate Direction of Transcription

Restriction Site and Functional Map of Plasmid pPR3
(7740 bp) Arrows Indicate Direction of Transcription Synthesis Procedure for Fragment T₁₅

Construction Route for Plasmid pThα1

STABILIZING AND SELECTING RECOMBINANT DNA HOST CELLS

CROSS-REFERENCE

This application is a continuation-in-part of copending application Ser. No. 193,556, filed Oct. 3, 1980, now abandoned.

SUMMARY OF THE INVENTION

The invention is a selective system that provides a means for stabilizing and selecting recombinant DNA host cells through the use of a lethal chromosomal marker which is repressed by a gene borne on a recombinant DNA cloning vector. This is particularly important because recombinant DNA cloning vectors such as plasmids, are often rapidly lost from bacterial populations and industrial scale fermentations may require more than $10^{16}$ cells. Therefore, once the recombinant DNA coding for the desired product is inserted in a plasmid, it is desirable if not essential, that the microorganism culture containing the plasmid be stabilized so that all the cells comprising the culture will contain the desired plasmid. This is crucial since recombinant plasmids with foreign DNA are notoriously unstable and often more than 90% of the cells in a population may not contain the recombinant plasmid after a culture has been grown overnight. Consequently the productive capacity is dramatically reduced because expression of desired genes is possible only in those cells which retain the plasmid.

Very few effective methods have been described for stabilization of recombinant plasmids and all have serious disadvantages. One method involves incorporating antibiotic resistance genes into recombinant plasmids and then adding the appropriate antibiotic to the culture medium. Cells retaining the plasmid with the antibiotic resistance gene are selected for and those which lose the plasmid are selected against and are therefore eliminated. The major disadvantage of this approach is that it requires production scale growth of antibiotic resistant bacteria, use of an expensive antibiotic in the fermentation medium, and subsequent purification to remove the antibiotic from the desired product.

Complementation of an auxotrophic mutation on the chromosome is the other known method for stabilization of recombinant plasmids. This approach severely restricts the composition of the fermentation medium and requires fermentation in a medium that does not contain the required nutrient of the host bacteria. Moreover, syntrophism may allow cells to continue growth after loss of the plasmid. Therefore, both types of selection depend on specific manipulation of the media. Such restrictions increase the cost of fermentation and limit the options available for improving productivity.

Alternative selections which are independent of media composition and which provide for maintenance of the recombinant DNA cloning vector under all conditions of fermentation are urgently needed. Cell suicide is adaptable to satisfy this need in that suicidal cells containing a lethal marker on a chromosome and a repressor or complementing gene on a recombinant DNA cloning vector can be constructed. Cells constructed to these specifications will die if they lose the vector. The present invention embodies this principle and consequently insures that all viable cells in a culture will carry the desired recombinant DNA cloning vector. This is particularly important because the potential productivity of such cultures is enhanced without any of the disadvantages as previously described. The present invention as illustrated herein, discloses a method for selecting and maintaining a plasmid-containing bacterial population through the use of a lethal chromosomal marker which is repressed by a plasmid borne gene.

For purposes of the present invention and as defined herein, a recombinant DNA cloning vector is any agent, including but not limited to recombinant plasmids, bacteriophages, and viruses, consisting of a DNA molecule to which one or more additional DNA segments can or have been added.

A repressor, as defined herein, is a gene which is located on a recombinant DNA cloning vector and which represses and prevents expression of a lethal or conditionally lethal gene in a chromosome of a host cell.

A functional polypeptide, as defined herein, is a recoverable bioactive entirely heterologous polypeptide or precursor, a recoverable bioactive polypeptide comprised of a heterologous polypeptide and a portion or whole of a homologous polypeptide, or a recoverable bioinactive fusion polypeptide comprised of a heterologous polypeptide and a bioinactivating homologous polypeptide which can be specifically cleaved.

A fused gene product, as defined herein, is a recoverable heterologous polypeptide which is fused with a portion or whole of a homologous polypeptide.

A marker, as defined herein, is a gene or combination of genes of known function and location on a chromosome or a recombinant DNA cloning vector.

DETAILED DESCRIPTION OF THE INVENTION

Figure 1:
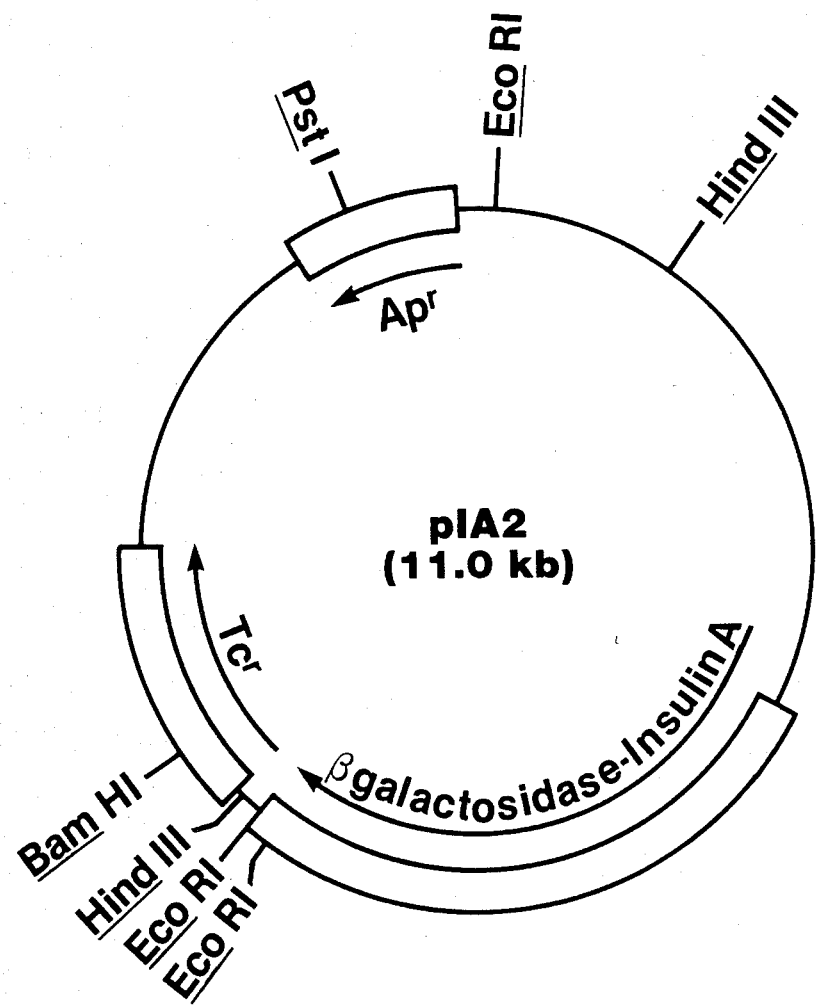

The present invention is a method for stabilizing and selecting host cells containing recombinant DNA which expresses a functional polypeptide comprising:
(a) transforming the host cells with a recombinant DNA cloning vector which contains both a repressor gene and a gene which expresses a functional polypeptide; and
(b) lysogenizing the transformed host cells with a lysogenic organism containing a marker which is lethal or conditionally lethal in the host cells but which is repressed in the transformed host cells by the repressor gene contained in the recombinant DNA cloning vector;

subject to the limitation that the recombinant DNA cloning vector contains a replicon and a promoter which are not sensitive to the repressor, and subject to the further limitation, that when the transformed host cells are lysogenized with a lysogenic organism containing a gene which is conditionally lethal, the resulting host cells are cultured under restrictive conditions.

As discussed herein above, the present invention can be used for the growth of cultures which produce products coded by recombinant DNA. Without an effective selective system, many cells in such cultures lose the desired plasmid and consequently production of the desired product is markedly reduced. Since the present invention insures that all viable cells in a culture will carry the recombinant DNA cloning vector, the potential productivity of the culture by use of the invention is enhanced.

The present invention is particularly versatile since it can be applied to the production of any substance where synthesis is determined by a recombinant DNA cloning vector. A preferred recombinant DNA cloning vector is the plasmid although bacteriophage and other vectors useful for illustrating the present invention will be apparent to those skilled in the art. The invention can also employ any lethal marker incorporated into a host cell chromosome if the lethality is counteracted or complemented by a marker incorporated onto a suitable recombinant DNA cloning vector. Since the usefulness of the present invention is independent of other markers that are cloned onto the cloning vector, the invention can be used with recombinant strains that carry one or more genes of commercial or research value.

The interaction of bacteriophage λ with E. coli K12 is employed to illustrate the applicability of cell suicide for maintaining and stabilizing recombinant DNA host cells. Bacteriophage λ is a temperate bacteriophage that follows either of two mutually exclusive cycles when infecting E. coli K12. In the lytic phase the bacteriophage DNA replicates autonomously, directs synthesis and assembly of bacteriophage components, and kills the cells concomitant with the release of mature bacteriophage. In the lysogenic phase the bacteriophage is integrated into the host's chromosome as a prophage, replicates as a marker on the chromosome, and blocks synthesis of bacteriophage components. A bacteriophage gene, λcI, codes for a repressor that maintains the lysogenic state and blocks expression of genes for bacteriophage components and maturation. If the repressor is inactivated or removed from the cell, the prophage educts from the chromosome, enters the lytic cycle, and kills the cell. Bacteriophage with a defective λcI gene cannot maintain the lysogenic state and are lethal to the cell unless a functional repressor is provided from an alternate source. In one illustrative embodiment of the present invention λcI90 is employed as a repressor dependent prophage and a cI gene, cloned into a recombinant DNA cloning vector, serves as the functional repressor.

Figure 2:
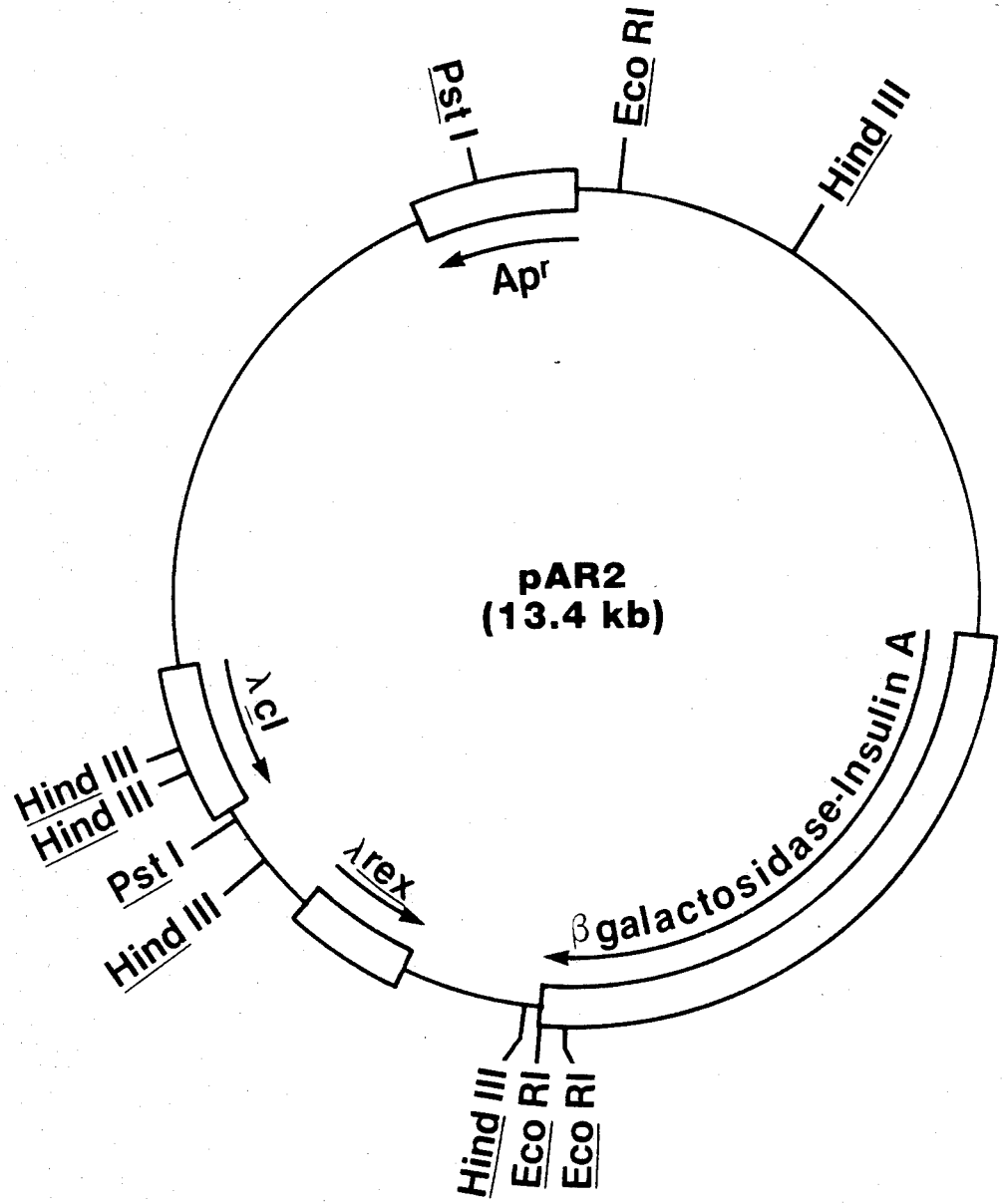

The selective system and usefulness of this invention can be shown by cloning the λcI857 repressor gene of bacteriophage lambda onto the insulin plasmid pIA2. Plasmid pIA2 is derived from pIA1 (disclosed in Goeddel et. al., 1979, Proc. Nat. Acad. Sci. 76:106–110) by the insertion of a tetracycline resistance marker. The insertion of tetracycline and other antibiotic resistance markers onto known plasmids is well understood in the art and can be accomplished readily by those with ordinary skill. A restriction site and functional map of plasmid pIA2 is presented in FIG. 1 of the accompanying drawings. The cloning of the λcI857 repressor gene of bacteriophage lambda onto plasmid pIA2 results in a novel plasmid, designated as pAR2, which blocks the lytic development of bacteriophage lambda and codes for the production of a fused gene product of human insulin A-chain. A restriction and functional map of plasmid pAR2 is presented in FIG. 2 of the accompanying drawings.

The novel pAR2 recombinant plasmid can be transformed into E. coli K12 RV308 (disclosed in Mauer et al., 1980, J. Mol. Biol. 139:147–161) and then the resulting strain can be lysogenized with bacteriophage λcI90. Since λcI90 does not produce a functional cI repressor, the constructed strain E. coli K12 RV308λcI90/pAR2 requires retention of the pAR2 plasmid whereas constructed strain E. coli K12 RV308/pAR2 survives equally well without the plasmid. A comparison of plasmid retention in the two strains clearly demonstrates that substantially all the viable cells in the strain with the invention have the desired plasmid. Moreover the E. coli K12 RV308λcI90/pAR2 strain not only maintains the pAR2 plasmid but also produces the desired fused gene product as detected by polyacrylamide gel electrophoresis.

Plasmid pAR2 can also be transformed into E. coli K12 C600$R_k$-$M_k$- (disclosed in Chang and Cohen, 1974, Proc. Nat. Acad. Sci. 71:1030–1034) and then the resulting strain can be lysogenized with bacteriophage λcI90. The constructed E. coli K12 C600$R_k$-$M_k$-λcI90/pAR2 strain thus requires the pAR2 plasmid for survival and therefore also exemplifies the present invention.

Other plasmids can also be used to further exemplify the present invention. For example, the cro gene of bacteriophage lambda can be cloned onto plasmid pBR322 (disclosed in Bolivar, 1979, Life Sci. 25:807–818) by the insertion of the BamHI-EcoRI fragment of bacteriophage λcI857. The new plasmid, designated as pAR1, can be transformed into E. coli K12 RV308 and then the resulting strain can be lysogenized with bacteriophage λcI90. A similar operation can also be performed using E. coli K12 C600$R_k$-$M_k$- or E. coli K12 C600 as the host and bacteriophage λcI857 as the lysogenic organism. Since the λcro gene produces a repressor that replaces the function of the cI repressor, it is readily apparent that constructed strains E. coli K12 RV308λcI90/pAR1, E. coli K12 C600$R_k$-$M_k$-λcI857-/pAR1 and E. coli K12 C600λcI857/pAR1 require the λcro containing plasmid for survival. However, since the λcI857 repressor is inactivated at 38°–44° C. or above (restrictive conditions) and is activated at lower temperatures (permissive conditions), the λcro containing plasmid is only required for survival in the latter strain under restrictive culture conditions. A comparison of plasmid retention in E. coli K12 C600$R_k$-$M_k$-λcI857/pAR1 under permissive condition and therefore without the present invention and under restrictive conditions and therefore with the present invention, clearly demonstrates that substantially all the viable cells in the culture with the invention have the desired plasmid. Also a comparison of plasmid retention in constructed strains E. coli K12 RV308λcI90/pAR1 with the invention and E. coli K12 RV308/pAR1 without the invention shows similar results. The use of plasmid pAR1 is particularly advantageous because the plasmid contains a promoter which is readily adaptable for the insertion of any one of a variety of genes coding for useful products.

Plasmids pPR1 and pPR3 were also constructed to further exemplify and demonstrate the broad application of the present invention. Plasmid pPR1 was constructed by inserting the 2.5 Kb BglII fragment of bacteriophage λcI857 into the unique BamHI restriction site of plasmid pIA7Δ4Δ1. A restriction site and functional map of pIA7Δ4Δ1 is presented in FIG. 3 of the accompanying drawings. As illustrated herein, pIA7Δ4Δ1 contains the E. coli tryptophan promoter, antibiotic resistance markers, and a gene which expresses a fused gene product comprising a portion of the trp E protein fused with the A polypeptide chain of human insulin.

Plasmid pIA7Δ4Δ1 is derived from pBR322 and is constructed according to the procedure disclosed in Example 13A-I herein. With regard to conventions, the symbol "Δ" connotes a deletion. Thus, for example, reference to a plasmid followed by, "ΔEcoRI-XbaI" describes the plasmid from which the nucleotide sequence between EcoRI and XbaI restriction enzyme sites has been removed by digestion with those enzymes. For convenience, certain deletions are denoted by number. Thus, beginning from the first base pair ("bp") of the EcoRI recognition site which precedes the gene for tetracycline resistance in the parental plasmid pBR322, "Δ1" connotes deletion of bp 1-30 (ie, ΔEcoRI-HindIII) and consequent disenabling of the tetracycline promoter/operator system; "Δ2" connotes deletion of bp 1-375 (ie, ΔEcoRI-BamHI) and consequent removal of both the tetracycline promoter/operator and a portion of the structural gene which encodes tetracycline resistance; and "Δ4" connotes deletion of bp ~900-~1500 from the trp operon fragment eliminating the structural gene for the trp D polypeptide.

Figure 4:
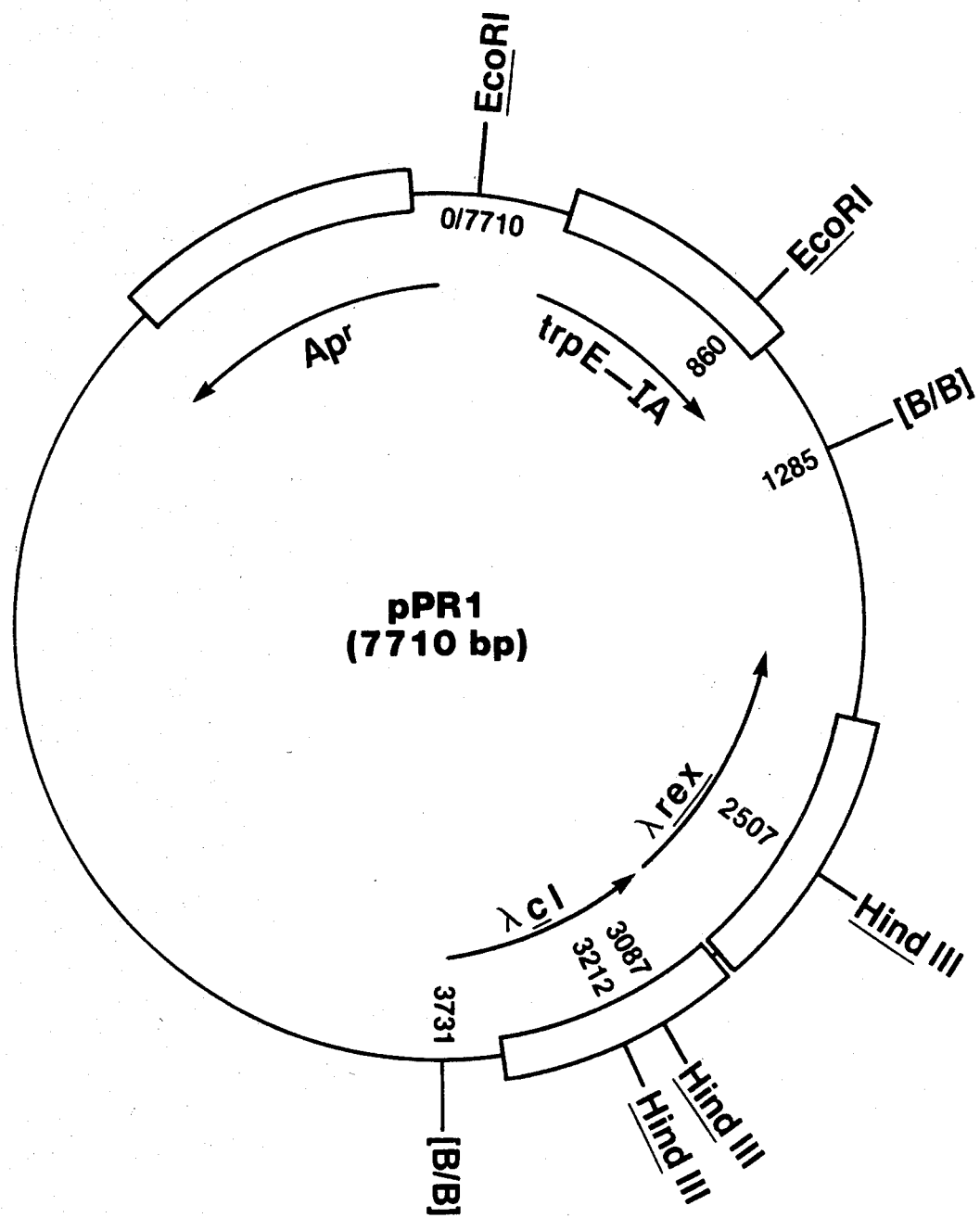

The cloning of the λcI857 repressor gene of bacteriophage lambda onto plasmid pIA7Δ4Δ1 results in a novel plasmid, designated as pPR1, which blocks the lytic development of bacteriophage lambda and concurrently codes for the production of the above aforementioned fused gene product. A restriction site and functional map of pPR1 is presented in FIG. 4 of the accompanying drawings. In the figure, the BglII-BamHI ligation sites are designated by the symbol '[B/B]'.

The novel pPR1 recombinant plasmid can be transformed, for example, into E. coli K12 RV308, E. coli K12 C600 (disclosed in Bachman, 1972, Bacteriol. Rev. 36:526-557), and E. coli K12 C600R$_k$-M$_k$- (disclosed in Chang and Cohen, 1974, Proc. Nat. Acad. Sci. 71:1030-1034) and then the resulting strains can be lysogenized with bacteriophage λcI90. Since λcI90 does not produce a functional cI repressor, the constructed strains E. coli K12 RV308λcI90/pPR1, E. coli K12 C600λcI90/pPR1 and E. coli K12 C600R$_k$-M$_k$-λcI90/pPR1 require retention of the pPR1 plasmid whereas constructed strains E. coli K12 RV308/pPR1, E. coli K12 C600/pPR1, and E. coli K12 C600R$_k$-M$_k$-/pPR1 survive equally well without the plasmid. A comparison of plasmid retention in the strains clearly demonstrates that substantially all the viable cells in the strains with the invention have the desired plasmid. Moreover, the E. coli K12 RV308λcI90/pPR1, E. coli K12 C600λcI90/pPR1, and E. coli K12 C600R$_k$-M$_k$-λcI90/pPR1 strains will also maintain the pPR1 plasmid and produce the desired fused gene product which can be detected by polyacrylamide gel electrophoresis.

Plasmid pPR3 was constructed by inserting the 2.5 Kb BglII fragment of bacteriophage λcI857 into the unique BamHI restriction site of plasmid pIB7Δ4Δ1. A restriction site and functional map of pIB7Δ4Δ1 is presented in FIG. 5 of the accompanying drawings. As illustrated herein, pIB7Δ4Δ1 contains a gene which expresses a fused gene product comprising a portion of the trp E protein fused with the B polypeptide chain of human insulin.

Plasmid pIB7Δ4Δ1 is derived from pBR322 in a way analogous to that described for pIA7Δ4Δ1. The specific construction is disclosed in Example 21 herein.

Figure 6:
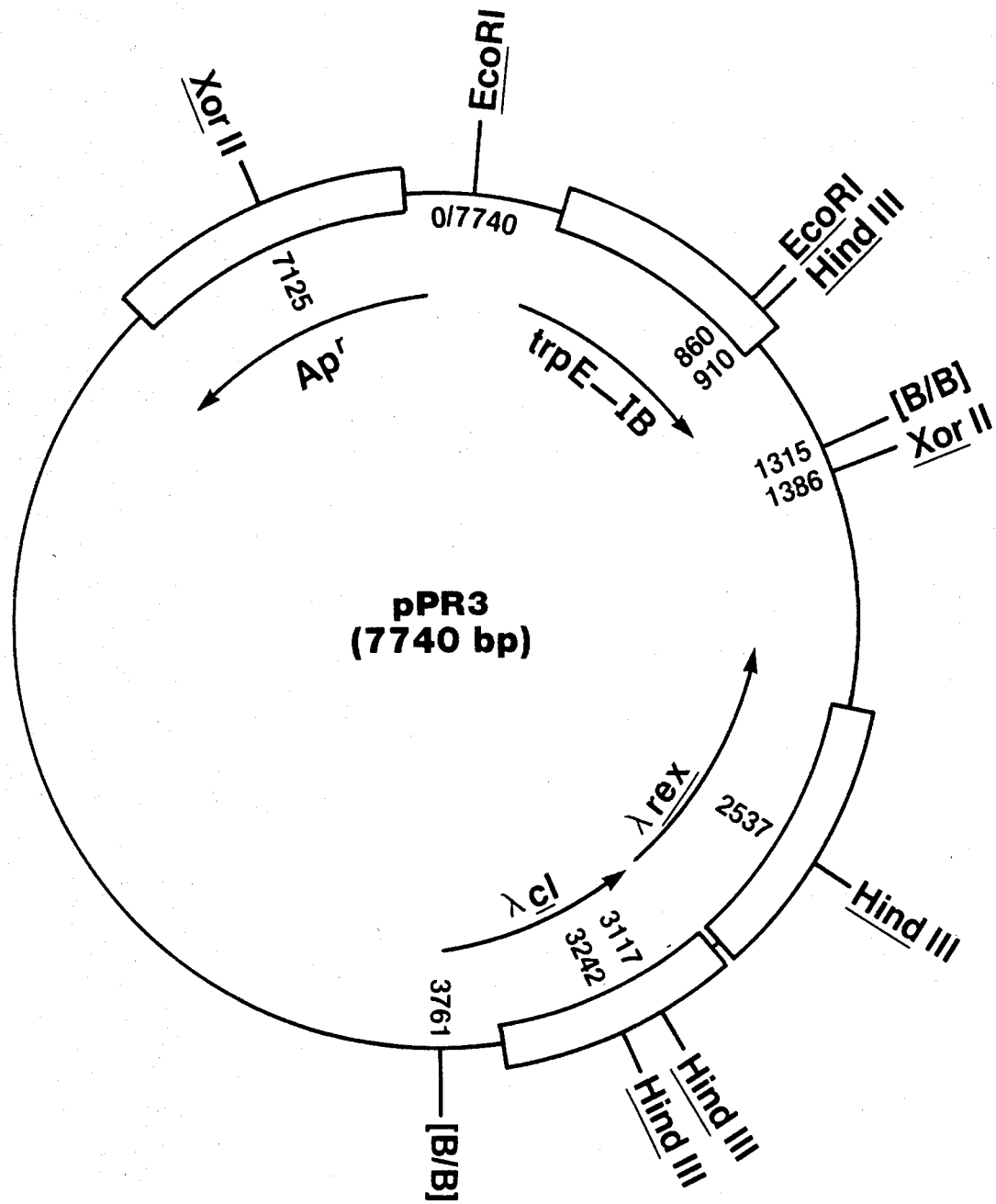

The cloning of λcI857 repressor gene of bacteriophage lambda onto pIB7Δ4Δ1 results in the novel plasmid pPR3. The latter plasmid blocks the lytic development of bacteriophage lambda and concurrently codes for the production of the above aforementioned fused gene product. A restriction site and functional map of pPR3 is presented in FIG. 6 of the accompanying drawings. In the figure, the BglII-BamHI ligation sites are designated by the symbol '[B/B]'.

The novel pPR3 recombinant plasmid can be transformed, for example, into E. coli K12 RV308, E. coli K12 C600, and E. coli K12 C600R$_k$-M$_k$- and then the resulting strains can be lysogenized with bacteriophage λcI90. As was previously described for the lysogenized pPR1 containing strains, the constructed E. coli K12 RV308λcI90/pPR3, E. coli K12 C600λcI90/pPR3, and E. coli K12 C600R$_k$-M$_k$-λcI90/pPR3 strains require retention of the pPR3 plasmid whereas constructed strains E. coli K12 RV308/pPR3, E. coli K12 C600/pPR3, and E. coli K12 C600R$_k$-M$_k$-/pPR3 do not and survive equally well without the plasmid. A comparison of plasmid retention in the strains clearly demonstrates that substantially all the viable cells in the strains with the invention have the desired plasmid. Moreover, the E. coli K12 RV308λcI90/pPR3, E. coli K12 C600λcI90/pPR3, and E. coli K12 C600R$_k$-M$_k$-λcI90/pPR3 strains will also maintain their plasmids and produce the desired fused gene product which can be detected by polyacrylamide gel electrophoresis.

The λcI857 repressor gene used herein to illustrate the present invention is temperature sensitive and is inactivated at 38° C. to 44° C. or above. A temperature shift to 38° C. to 44° C. therefore lyses the cells by inducing the lytic cycle of the lambda prophage which, in accordance with the present invention, has been incorporated into the host cell strain. As is readily apparent, when a temperature sensitive repressor which represses a lethal or conditional lethal marker that causes host cell lysis is used and when the host cells are cultured at a temperature which inactivates the repressor and, in the case of a conditional lethal marker, at a temperature which is not within the temperature range for permissive culture of the host cells, the present invention also provides a simple, convenient, and inexpensive method to lyse cells for purification of intracellular products.

A further illustrative embodiment of the above method for lysing recombinant DNA containing host cells comprises lysogenizing the host cells with a lysogenic organism containing a conditional lethal marker which causes host cell lysis and culturing the host cells under restrictive conditions. Furthermore, an additional example of this method for lysing host cells comprises transforming the host cells with a recombinant DNA cloning vector which contains a conditional lethal marker which causes host cell lysis and culturing the transformed host cells under restrictive conditions. The culturing of host cells under restrictive conditions can be carried out easily during culture any time that host cell lysis is desired.

As illustrated herein, a preferred embodiment of the present invention employs a plasmid borne gene to repress a lethal chromosomal marker. Selection of cells is independent of the replicon and also the other genes on the plasmid. Furthermore, although the embodiment herein described employs the bacteriophage λcI857 gene, any other λcI gene that produces a functional repressor can be used. Other repressor genes, such as, for example, the λcro gene can also be used since, as described above, it produces a repressor that can replace the function of the cI repressor. The prophage used to exemplify the present invention carries a λcI90 mutation and consequently does not produce a functional λcI repressor. Other bacteriophage λ mutants can also be employed if they too lack a functional cI gene or repressor; as is readily apparent, such mutants require an alternate source of repressor to maintain the lysogenic state.

The selective system of the present invention can be imposed on host cells containing plasmids with genes that express a variety of useful products. For example, the plasmid borne gene may be a naturally occurring gene, non-naturally occurring gene, or a gene which is in part naturally occurring and in part synthetic or non-naturally occurring. More particularly, the invention can be used to select and maintain cells containing a plasmid borne gene coding for human pre-proinsulin, human proinsulin, human insulin A-chain, human insulin B-chain, human growth hormone, non-human growth hormone, nonhuman insulin, human interferon, nonhuman interferon, viral antigen, urokinase, any peptide hormone, any enzyme, any polypeptide, or for virtually any other gene with research or commercial value.

In the specific embodiments of the invention described herein, plasmid replication and expression of the gene product are determined respectively by the replicon from pMB1 (disclosed in Bolivar, 1979, Life Sci. 25:807–818) and by either the lac or the trp promoter. Other replicons and promoters can also be used so long as they are functional in $E.$ $coli$ K12 and are not sensitive to the particular repressor being used. It is understood that those skilled in the art know or readily can determine which replicons and promoters are functional in $E.$ $coli$ K12 and which are not sensitive to a particular repressor. Examples of other replicons include but are not limited to replicons from ColE1, NR1, RK2, RK6, pSC101, RP1, RP4, F, and the like, including bacteriophage that replicate in $E.$ $coli$ K12. Examples of other promoters include but are not limited to the bacteriophage λ $P_L'$ promoter, lipoprotein promoter, ribosomal protein or RNA promoters, and virtually any other promoter. It is understood that other replicons and promoters can be constructed and will be apparent to those skilled in the art.

The present invention as stated above and illustrated herein, discloses a method for selecting and maintaining a plasmid-containing bacterial population through use of a lethal chromosomal marker which is repressed by a plasmid borne gene. Many embodiments of this invention are possible. For example, various bacteriophage can be substituted for bacteriophage λ and other classes of lethal mutations can be used so long as they are repressed by a plasmid borne gene. Illustrative examples of lethal mutations that are useful in accordance with the present invention include but are not limited to the following: chromosomal DNA replication, cell wall synthesis, ribosome function, RNA polymerase, tRNA synthesis and modification, aminoacyl tRNA synthetase, DNA restriction and modification, and cell division mutations. Other lethal mutations will be apparent to those skilled in the art.

Many classes of lethal mutations, identified as conditional lethal mutations, are expressed only under restrictive conditions, such as for example, elevated temperature. Such mutations can be isolated and are lethal to cells when expressed but are not expressed or lethal under certain permissive culture conditions. Cell suicide of the present invention can be employed under restrictive conditions with any conditional lethal mutation so long as a plasmid, or other recombinant DNA cloning vector, carries an appropriate repressor which is functional under restrictive conditions. Such a mutation would not again become conditionally lethal unless the plasmid, or other recombinant DNA cloning vector, was lost.

Nonsense mutations and repressors represent a special class of genes that can be employed to illustrate the stabilization and selection as described in the present invention. A nonsense mutation is a base substitution or frameshift mutation that converts an amino acid specifying codon into a chain terminating codon. Consequently nonsense mutations result in the premature termination of a polypeptide chain at the point where the nonsense codon occurs in the messenger ribonucleic acid (mRNA). A nonsense repressor is a gene that allows the insertion of an amino acid into the growing polypeptide chain in response to a nonsense codon. In the absence of such a nonsense repressor, a nonsense mutation causes a polypeptide termination. To further exemplify the present invention, a lethal nonsense mutation can be incorporated into a chromosome of a transformed host cell if a suitable nonsense repressor is cloned onto the recombinant DNA cloning vector within the host cell. A genetic balance is thus maintained unless the recombinant DNA cloning vector is lost at which time the host cell loses viability and self destructs.

The wealth of genetic and biochemical information about $E.$ $coli$ K12 makes it a convenient host cell for purposes of the present invention. However, the invention is not limited to any one genus, species or strain but can be used with any organism where lethal mutations and repressors are available or can be isolated or constructed. For example, the invention is applicable to prokaryotes, free living eukaryotes susceptible to culture, and more particularly, to bacteria, including but not limited to Bacillus, $Bacillus$ $subtilis,$ Staphylococcus, Streptococcus, Actinomycetes, Streptomyces, Serratia, Agrobacterium, and Pseudomonas; fungi, including but not limited to Neurospora, Cephalosporium, Aspergillus, Penicillium, and yeast; and cells susceptible to culture which are derived from tissue of multicellular organisms, including but not limited to Chordata, Mammalia, Aves, Amphibia, Reptilia, or plants.

All of the embodiments of the present invention share the common feature that they are insensitive to media composition. Therefore, the invention allows for a wide range of fermentation manipulation to improve productivity.

The following examples further illustrate and also present a preferred embodiment of the invention disclosed herein. Both an explanation of and the actual procedures for constructing the invention are described where appropriate.

EXAMPLE 1

Construction of Recombinant Plasmid pAR2

The several BglII restriction sites in bacteriophage λcI857 and a single BamHI restriction site in plasmid pIA2 allow for the cloning of bacteriophage fragments into the pIA2 cloning vector. Bacteriophage λcI857 contains six sites that are sensitive to BglII. One of the BglII fragments contains 2.5 Kb including the λcI gene and also the λrex gene (Szybalski and Szybalski, 1979, Gene 7:217–280 and O'Brien, ed., March 1980, Genetic Maps, Vol. 1, NIH). BglII fragments contain 5' extensions with the sequence GATC that are identical and complementary to 5' extensions on BamHI fragments. Human insulin plasmid, pIA2 contains 11.0 Kb including a single site that is cleaved by BamHI. Cloning into the BamHI site inactivates the Tc resistance gene carried on pIA2. Ligation of BglII fragments and BamHI fragments produces recombinants with the sequences

| AGATCC | | GGATCT |
|--------|---|--------|
| TCTAGG | or | CCTAGA | at the junctions. These sequences are not cleaved by BglII or BamHI. Therefore, restriction with both enzymes eliminates all ligation products except those containing a λBglII fragment ligated into the BamHI site of pIA2.

Restriction enzymes were purchased from commercial sources and were used according to instructions supplied by the manufacturer.* Recombinant DNA molecules were formed with T4 DNA ligase in a 0.10 ml. reaction mixture containing $3.0 \times 10^{-13}$ moles restricted vector and $6.0 \times 10^{-13}$ moles of bacteriophage λ restriction fragments. Other and more complete reaction conditions are as disclosed in Tanaka and Weissblum, 1975, J. Bacteriol., 121:354–362.

*Restriction enzymes and instructions can be readily obtained from the following sources:
Bethesda Research Laboratories Inc., Box 6010, Rockville, Md. 20850
Boehringer Mannheim Biochemicals, 7941 Castleway Drive, P.O. Box 50816 Indianapolis, Ind. 46250
Research Products, Miles Laboratories Inc., Elkhart, Ind. 46515

EXAMPLE 2

Transformation of Recombinant Plasmid pAR2 Into *E. coli* K12 C600$R_K$-$M_K$-

Fresh overnight cultures of *E. coli* K12 C600$R_K$-$M_K$- (disclosed in Chang and Cohen, 1974, Proc. Nat. Acad. Sci. 71:1030–1034) were subcultured 1:10 in fresh L-broth (disclosed in Miller, 1972, Experiments in Molecular Genetics, Cold Spring Harbor Labs, Cold Spring Harbor, N.Y.) and grown at 37° C. for 1.0 hr. A total of 660 Klett units of cells were harvested, washed with 2.5 ml of 100 mM NaCl, suspended in 150 mM CaCl$_2$ with 10.0% glycerol, and incubated at room temperature for 20 min. The cells were harvested by centrifugation, resuspended in 0.5 ml of CaCl$_2$-glycerol, chilled on ice for 3–5 minutes and frozen. The suspensions of cells were stored in liquid nitrogen until use. Preservation and storage did not adversely affect the viability or frequency of transformation by covalently closed circular DNA. The cells were thawed in an ice bath and mixed in a ratio of 0.1 ml of cells to 0.05 ml of DNA (prepared according to the teaching of Example 1) at a concentration of 2.0 µg/ml. The samples thus prepared were chilled on ice for 10.0 minutes, and were then diluted with 0.85 ml of L-broth, incubated at 32° C. for 2.0 hr, spread on L-agar (disclosed in Miller, 1972) with $5 \times 10^9$ λb2, and incubated at 32° C. Transformants were selected for immunity to bacteriophage λb2 at 32° C. The recombinants were tested to verify Ap$^r$, Tc$^s$, λb2 immunity at 32° C., and λb2 sensitivity at 42° C. One transformant was selected and designated *E. coli* K12 C600$R_K$-$M_K$-/pAR2. This surviving colony was tested for the expected phenotypes and used for isolation and amplification of the constructed recombinant plasmid pAR2.

EXAMPLE 3

Amplification and Isolation of Recombinant Plasmid pAR2

The plasmid DNA of *E. coli* K12 C600$R_K$-$M_K$-/pAR2 was amplified with chloramphenicol and isolated by cleared lysate procedure (disclosed in Bazaral and Helinski, 1968, J. Mol. Biol. 36:185–194). The covalently closed circular DNA was purified by equilibrium ultracentrifugation in CsCl and propidium di-iodide. The propidium di-iodide was extracted with 2-propanol and the DNA was stored in CsCl at −20° C. Working solutions of DNA were exchanged into SSC/10 buffer (0.015 M NaCl, 0.0015 M sodium citrate pH 7.0) by chromatography on Sephadex (PD10*) columns.

*Available from Pharmacia, 800 Centennial Ave, Piscataway, N.J. 08851.

EXAMPLE 4

Transformation of Recombinant Plasmid pAR2 Into *E. coli* K12 RV308

Transformation of recombinant plasmid pAR2 into *E. coli* K12 RV308 was carried out according to the procedure taught in Example 2 except that 300 mM CaCl$_2$ was employed. Samples were diluted with 0.85 ml. of L-broth, incubated at 32° C. for 2.0 hr, spread on L-agar with $5 \times 10^9$ λb2, and incubated at 32° C. Surviving colonies were tested for the expected phenotypes and constituted the desired *E. coli* K12 RV308/pAR2 transformants.

EXAMPLE 5

Construction of *E. coli* K12 RV308λcI90/pAR2 by Lysogenization with λcI90

*E. coli* K12 RV308/pAR2 (prepared according to the teaching of Example 4) was grown at 32° C. until 35 Klett units and was then transferred to 45° C. for 60.0 minutes. The cells were infected with λcI90 at an moe of 20 and incubated at 45° C. for 40 minutes. Colonies were grown at 32° C. on L-agar containing 10 µg/ml. ampicillin. The resulting *E. coli* K12 RV308λcI90-/pAR2 colonies were tested to verify growth at 32° C. and sensitivity at 42° C.

EXAMPLE 6

Construction of Recombinant Plasmid pAR1

The EcoR1 and BamHI restriction sites in bacteriophage λcI857 and plasmid pBR322 allow for the cloning of bacteriophage fragments onto the pBR322 cloning vector. Restriction enzymes were purchased from commercial sources and were used according to instructions supplied by the manufacturer. Accordingly, bacteriophage λcI857 and plasmid pBR322 were each double treated with restriction enzymes EcoR1 and BamHI. About 528 µg of the thus prepared restricted λcI857 DNA in 10 mM Tris-HCl at about pH 8 was incubated with 10,000 units/ml of bacterial alkaline phosphatase at 65° C. for 30 minutes. Bacterial alkaline phosphatase removes the terminal phosphate groups from the bacteriophage lambda restriction fragments and thereby prevents their ligation to each other. This enzymatic treatment however, does not prevent ligation to non-treated DNA such as, for example, restricted plasmid pBR322.

The treated bacteriophage λcI857 restricted DNA was purified by equilibrium ultracentrifugation in CsCl and propidium di-iodide. The propidium di-iodide was extracted with 2-propanol and the DNA was stored in CsCl at −20° C. Working solutions of DNA were exchanged into SSC/10 buffer (0.015M NaCl, 0.0015M sodium citrate, pH 7) by chromatography on Sephadex (PD10) columns.

Recombinant DNA molecules were formed with T4 DNA ligase in a 0.10 ml. reaction mixture containing 2.2 μg of restricted pBR322 vector and 3.8 μg of bacteriophage lambda restriction fragments. Other and more complete reaction conditions are as disclosed in Tanaka and Weisblum, 1975, J. Bacteriol., 121:354–362.

EXAMPLE 7

Transformation of Recombinant plasmid pAR1 Into E. coli K12 C600$R_k$-$M_k$-

Transformation of plasmid pAR1 into E. coli K12 C600$R_k$-$M_k$- is carried out according to the procedure taught in Example 2. Because the λcro repressor is not temperature sensitive, the transformants were selected for immunity to bacteriophage λb2 at both 32° and 42° C. The recombinants were further tested to verify $Ap^r$ and $Tc^s$ and one of the transformants was selected and designated E. coli K12 C600$R_k$-$M_k$-/pAR1. This surviving colony was tested for the expected phenotypes and was used for isolation and amplification of the recombinant plasmid pAR1. Both the isolation and amplification steps were carried out according to the procedure taught in Example 3.

EXAMPLE 8

Construction of E. coli K12 RV308λcI90/pAR1 by Lysogenization with λcI90

E. coli K12 RV308/pAR1 (transformation of plasmid pAR1 into E. coli K12 RV308 was carried out according to the procedure taught in Example 4) was grown at 32° C. until 35 Klett units and was then transferred to 45° C. for 30.0 or 60.0 minutes. The cells were then infected with λcI90 at an moe of 20 and incubated at 45° C. for 40 minutes. Colonies were grown at 32° C. on L-agar containing 10 μg/ml. ampicillin. The resulting E. coli K12 RV308λcI90/pAR1 colonies were tested for the expected phenotype and in this way the genotype of the constructed strain was confirmed.

EXAMPLE 9

Construction of E. coli K12 C600$R_k$-$M_k$-λcI857/pAR1 by Transformation with pAR1

E. coli K12 C600$R_k$-$M_k$-λcI857 (constructed according to Miller, 1972) was rendered competent and transformed according to the procedure taught in Example 2 except that the cells were grown at 32° rather than 37° C. Colonies were grown on L-agar containing 10 μg/ml ampicillin and the resulting E. coli K12 C600$R_k$-$M_k$-λcI857/pAR1 colonies were tested for the expected phenotype and in this way the genotype of the desired strain was confirmed.

EXAMPLE 10

Construction of E. coli K12 C600λcI90/pAR2

The desired strain is constructed in substantial accordance with the teaching of Examples 1, 2, and 5, except that E. coli K12 C600, rather than E. coli K12 RV308, is used as the host strain.

EXAMPLE 11

Construction of E. coli K12 C600λcI857/pAR1

The desired strain is constructed in substantial accordance with the teaching of Examples 6, 7, and 9 except that E. coli K12 C600, rather than E. coli K12 C600$R_k$-$M_k$-, is used as the host strain.

EXAMPLE 12

Method For Determining Stabilities of Host Cells Containing Recombinant Plasmids With and Without Selection The $Ap^r$ gene on the recombinant plasmids was employed to assay the frequency of cells containing the plasmids. Serial dilutions of culture were spread on L-agar and grown at 32° C. with and without 10 μg/ml of ampicillin. The frequency of plasmid+ cells was taken as the ratio of ampicillin resistant colonies to the total number of colonies that grew on L-agar without ampicillin. Alternately, the colonies on L-agar were replica plated to L-agar with 10 μg/ml of ampicillin and grown at 32° C. The frequency of plasmid+ cells was taken as the ratio of ampicillin resistant colonies to the total number of colonies that grew on L-agar without ampicillin.

EXAMPLE 13

Construction of Plasmid pIA7Δ4Δ1

A. Construction of Plasmid pBRHtrp

Plasmid pGM1 carries the E. coli tryptophan operon containing the deletion ΔLE1413 (Miozzari, et al., 1978, J. Bacteriology, 1457–1466) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. E. coli K12 W3110tna2trp-Δ102/pGM1 has been deposited with the American Type Culture Collection (ATCC No. 31622) and pGM1 may be conventionally removed from the strain for use in the procedures described below.

About 20 μg. of the plasmid were digested with the restriction enzyme PvuII which cleaves the plasmid at five sites. The gene fragments were next combined with EcoRI linkers (consisting of a self complementary oligonucleotide of the sequence: pCATGAATTCATG) providing an EcoRI cleavage site for later cloning into a plasmid containing an EcoRI site. The 20 μg of DNA fragments obtained from pGM1 were treated with 10 units $T_4$ DNA ligase in the presence of 200 pico moles of the 5'-phosphorylated synthetic oligonucleotide pCATGAATTCATG and in 20 μl $T_4$ DNA ligase buffer (20 mM tris, pH 7.6, 0.5 mM ATP, 10 mM $MgCl_2$, 5 mM dithiothreitol) at 4° C. overnight. The solution was then heated 10 minutes at 70° C. to halt ligation. The linkers were cleaved by EcoRI digestion and the fragments, now with EcoRI ends, were separated using 5 percent polyacrylamide gel electrophoresis (herein after "PAGE"). The three largest fragments were isolated from the gel by first staining with ethidium bromide and then locating the fragments with ultraviolet light and cutting from the gel the portions of interest. Each gel fragment, with 300 microliters 0.1xTBE, was placed in a dialysis bag and subjected to electrophoresis at 100 v for one hour in 0.1xTBE buffer (TBE buffer contains: 10.8 gm tris base, 5.5 gm boric acid, 0.09 gm $Na_2EDTA$ in 1 liter $H_2O$). The aqueous solution was collected from the dialysis bag, phenol extracted, chloroform extracted, and made 0.2M with respect to sodium chloride. The DNA was then recovered in water after ethanol precipitation. The trp promoter/operator-containing gene with EcoRI sticky ends was identified in the procedure next described, which entails the insertion of fragments into a tetracycline sensitive plasmid which, upon promoter/operator insertion, becomes tetracycline resistant. All DNA fragment isolations hereinafter described are performed using PAGE followed by the electroelution method described above.

B. Construction of Plasmid pBRH trp Expressing Tetracycline Resistance Under the Control of the Trp Promoter/Operator and Identification and Amplification of the Trp Promoter/Operator Containing DNA Fragment Isolated in 'A' above.

Plasmid pBRH1, (Rodriguez, et al., 1979, Nucleic Acids Research 6, 3267–3287) expresses ampicillin resistance and contains the gene for tetracycline resistance but, there being no associated promoter, does not express that resistance. The plasmid is accordingly tetracycline sensitive. By introducing a promoter/operator system in the EcoRI site, the plasmid can be made tetracycline resistant.

Plasmid pBRH1 was digested with EcoRI. The enzyme was removed by phenol extraction followed by chloroform extraction and then the DNA was recovered in water after ethanol precipitation. The resulting DNA molecule was, in separate reaction mixtures, combined with each of the three DNA fragments obtained in Example 13A above and ligated with T4 DNA ligase as previously described. The DNA present in the reaction mixture was used to transform competent *E. coli* K12 strain 294, (Backman et al., 1976, Proc. Nat. Acad. Sci. USA 73:4174–4198, ATCC No. 31448) by standard techniques (Hershfield et al., 1974, Proc. Nat. Acad. Sci. USA 71:3455–3459) and the bacteria were then plated on LB plates (Miller, 1972) containing 20 µg/ml ampicillin and 5 µg/ml tetracycline.

Several tetracycline-resistant colonies were selected and the plasmid DNA was isolated and designated pBRHtrp. The presence of the desired fragment was confirmed by restriction enzyme analysis. Plasmid pBRH trp expresses β-lactamase, imparting ampicillin resistance, and contains a DNA fragment which includes the trp promoter/operator. The DNA fragment also codes for a first protein, (designated LE'), comprising a fusion of the first six amino acids of the trp leader and approximately the last third of the trp E polypeptide, a second protein (designated D'), corresponding to approximately the first half of the trp D polypeptide, and a third protein, coded for by the tetracycline resistance gene.

C. Construction of Plasmid pSOM7Δ2

Plasmid pBRHtrp was digested with EcoRI restriction enzyme and the resulting fragment, isolated by PAGE and electroelution, was combined with EcoRI-digested plasmid pSOM11 (Itakura et al., 1977, Sci. 198:1056, G. B. Patent Publication No. 2,007,676A). The mixture was ligated with T4 DNA ligase and the resulting DNA transformed into *E. coli* K12 strain 294 as previously described. Transformant bacteria were selected on ampicillin-containing plates and the resulting ampicillin-resistant colonies were screened by colony hybridization (Gruenstein et al., 1975, Proc. Nat. Acad. Sci. USA 72:3951–3965). The trp promoter/operator-containing fragment, isolated from pBRH trp and then radioactively labelled with $p^{32}$, was used as a probe in the above procedure. Several colonies were shown to be positive by colony hybridization and were therefore selected. Plasmid DNA was isolated and the orientation of the inserted fragments was determined by restriction analysis, using enzymes BglII and BamHI in double digestion. Colonies containing the desired plasmid with the trp promoter/operator fragment in the proper orientation were grown in LB medium (Miller, 1972) containing 10 µg/ml ampicillin. The desired plasmid was designated pSOM7Δ2 and was used for subsequent constructions described below.

D. Construction of Plasmid pTrp24

1. Construction of a Gene Fragment Comprising Codons for the Distal Regions of the LE' Polypeptide With BglII and EcoRI Restriction Sites Respectively at the 5' and 3' Ends of the Coding Strand Plasmid pSOM7Δ2 was HindIII digested followed by digestion with lambda exonuclease (a 5' to 3' exonuclease) under conditions chosen so as to digest beyond the BglII restriction site within the LE' encoding region. About 20 µg of HindIII-digested pSOM7Δ2 was dissolved in buffer (20 mM glycine buffer, pH 9.6, 1 mM MgCl$_2$, 1 mM β-mercaptoethanol). The resulting mixture was treated with 5 units of lambda exonuclease for 60 minutes at room temperature. The reaction mixture obtained was then phenol extracted, chloroform extracted, and ethanol precipitated.

To create an EcoRI residue at the distal end of the LE' gene fragment, a primer $^{32}$pCCTGTGCATGAT was synthesized by the improved phosphotriester method (Crea et al., 1978, Proc. Nat. Acad. Sci. USA 75:5765) and hybridized to the single stranded end of the LE' gene fragment resulting from lambda exonuclease digestion. The hybridization was performed by dissolving 20 µg of the lambda exonuclease-treated HindIII digestion product of plasmid pSOM7Δ2 in 20 µl H$_2$O and combining with 6 µl of a solution containing approximately 80 picomoles of the 5'-phosphorylated oligonucleotide described above. The synthetic fragment was hybridized to the 3' end of the LE' coding sequence and the remaining single strand portion of the LE' fragment was filled in by Klenow Polymerase I using dATP, dTTP, dGTP and dCTP. Klenow Polymerase I is the fragment obtained by proteolytic cleavage of DNA Polymerase I. It contains the 5'→3' polymerizing activity, the 3'→5' exonucleolytic activity, but not the 5'→3' exonucleolytic activity of the parental enzyme (Kornberg, 1974, W. H. Freeman and Co., SFO, 98).

The reaction mixture was thus heated to 50° C. and let cool slowly to 10° C., whereafter 4 µl of Klenow enzyme were added. After 15 minutes incubation at room temperature, followed by 30 minutes incubation at 37° C., the reaction was stopped by the addition of 5 µl of 0.25 molar EDTA. The reaction mixture was phenol extracted, chloroform extracted, and ethanol precipitated. The DNA was subsequently cleaved with the restriction enzyme BglII and the fragments were separated by PAGE. An autoradiogram obtained from the gel revealed a $^{32}$P-labelled fragment of the expected length of approximately 470 bp, which was recovered by electroelution. As outlined, this fragment LE'(d) has a BglII terminus and a blunt end coinciding with the beginning of the primer.

2. Construction of Plasmid pThα1

Plasmid pThα1 was constructed by inserting a synthesized gene for thymosin alpha 1 into plasmid pBR322. The synthesis of the thymosin alpha 1 coding DNA involves the synthesis and subsequent ligation of the 16 oligonucleotides ($T_1$ through $T_{16}$) that are indicated by the double headed arrows in FIG. 7 of the accompanying drawings. A Met codon ATG was inserted at the N-terminus and the 5' ends were designed with single-stranded cohesive termini to facilitate joining to plasmids cleaved with EcoR1 and BamH1. As can be readily appreciated, the BglII site in the center of the gene assists in the analysis of recombinant plasmids.

Oligodeoxyribonucleotides $T_1$ to $T_{16}$ were synthesized by the modified phosphotriester method using fully protected trideoxyribonucleotide building blocks (Itakura et al., 1977, Science 198:1056, and Crea et al., 1978). The various oligodeoxyribonucleotides are shown below in Table 1.

TABLE 1

SYNTHETIC OLIGONUCLEOTIDES FOR THYMOSINα1 GENE

| Compound | Sequence | Length | HPLC Analysis Retention Time (min)* |
|---|---|---|---|
| $T_1$ | A-A-T-T-C-A-T-G-T-C | 10 | 17.4 |
| $T_2$ | T-G-A-T-G-C-T-G-C-T-G-T-T-G-A | 15 | 24.3 |
| $T_3$ | T-A-C-T-T-C-T-T0C-T-G-A | 12 | 20.3 |
| $T_4$ | G-A-T-T-A-C-T-A-C-T-A-A-A | 13 | 22.0 |
| $T_5$ | G-C-A-G-C-A-T-C-A-G-A-C-A-T-G | 15 | 24.8 |
| $T_6$ | G-A-A-G-T-A-T-C-A-A-C-A | 12 | 20.1 |
| $T_7$ | A-G-T-A-A-T-C-T-C-A-G-A-A | 13 | 22.6 |
| $T_8$ | A-A-G-A-T-C-T-T-T-A-G-T | 12 | 20.2 |
| $T_9$ | G-A-T-C-T-T-A-A-A-G-G-A-G | 12 | 20.4 |
| $T_{10}$ | A-A-G-A-A-A-G-G-A-A-G-T-T | 12 | 21.1 |
| $T_{11}$ | G-T-C-G-A-A-G-A-G-G-C-T | 12 | 20.5 |
| $T_{12}$ | G-A-G-A-A-C-T-A-A-T-A-G | 12 | 20.4 |
| $T_{13}$ | C-T-T-C-T-T-C-T-C-C-T-T | 12 | 19.9 |
| $T_{14}$ | T-T-C-G-A-C-A-A-C-T-T-C | 12 | 20.5 |
| $T_{15}$ | G-T-T-C-T-C-A-G-C-C-T-C | 12 | 20.2 |
| $T_{16}$ | G-A-T-C-C-T-A-T-T-A | 10 | 17.2 |

*at ambient temperature

Figure 8:
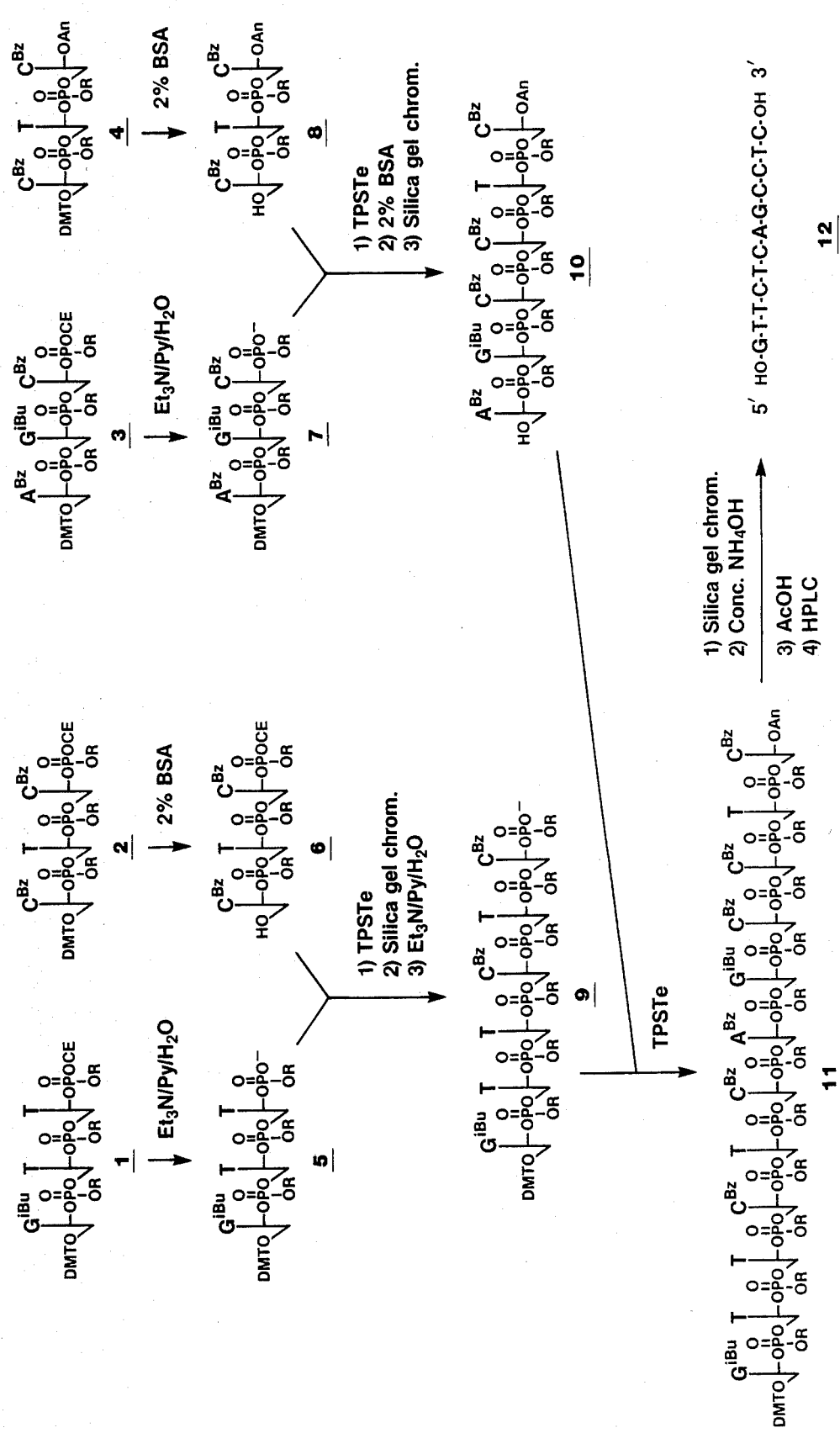

The above synthesis is typified by the following procedure for fragment $T_{15}$ as summarized in FIG. 8 of the accompanying drawings. Various nucleotide fragments that are used in the synthesis of T15 are numerically designated in the Figure. The abbreviations employed are as follows: TPSTe, 2,4,6-triisopropylbenzenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; An, anisoyl; iBu, isobutryl; Py, pyridine; AcOH, acetic acid; $Et_3N$, triethylamine.

The fully protected trideoxyribonucleotides 4 (85 mg, 0.05 mmol) and 2 (180 mg, 0.1 mmol) were deblocked at the 5' hydroxyls by treatment with 2% BSA in 7:3 (v/v) chloroform/methanol (10 and 20 ml, respectively) for 10 minutes at 0° C. Reactions were stopped by addition of saturated aqueous ammonium bicarbonate (2 ml), extracted with chloroform (25 ml) and washed with water (2×10 ml). The organic layers were dried (magnesium sulfate), concentrated to small volumes (about 5 ml) and precipitated by addition of petroleum ether (35°–60° C. fraction). The colorless precipitates were collected by centrifugation and dried in a dessicator in vacuo to give 6 and 8, respectively, each homogeneous by silica gel tlc (Merck 60 F254, chloroform/methanol, 9:1).

Trimers 1 and 3 (270 mg, 0.15 mmol; 145 mg, 0.075 mmol) were converted into their phosphodiesters (5 and 7) by treatment with triethylamine/pyridine/water (1:3:1, v/v, 10 ml) for 25 minutes at ambient temperature. Reagents were removed by rotary evaporation and the residues dried by repeated evaporations with anhydrous pyridine (3×10 ml). Trimer 8 (0.05 mmol) and trimer 7 were combined with TPSTe (50 mg, 0.15 mmol) in anhydrous pyridine (3 ml) and the reaction mixture left in vacuo at ambient temperature for two hours. TLC analysis showed that 95% of the trimer 8 had been converted into hexamer product (visualized by detection of the DMT group by spraying with 10% aqueous sulfuric acid and heating at 60° C.). The reaction was quenched by addition of water (1.0 ml) and the solvent evaporated under reduced pressure. After removal of pyridine by coevaporations with toluene, the hexamer was deblocked at the 5' position with 2% BSA (8 ml) as described above for trimers 4 and 2. The product (10) was purified on a silica gel column (Merck 60 H, 3.5×5 cm) by step gradient elution with chloroform/methanol (98:2 to 95:5, v/v). Fractions containing product 10 were evaporated to dryness.

Similarly, trimer 5 was coupled to 6 and the fully protected product directly purified on silica gel. This latter compound was deblocked at the 3' end by triethylamine/pyridine/water as described above to give fragment 9.

Finally, hexamers 9 and 10 were coupled in anhydrous pyridine (2 ml) with TPSTe (75 mg, 0.225 mmol) as the condensing agent. Upon completion (4 hours, ambient temperature) the mixture was rotary evaporated and the residue chromatographed on silica gel. Product 11 (160 mg) was obtained by precipitation with petroleum ether and appeared homogeneous on TLC. A portion of compound 11 (20 mg) in pyridine (0.5 ml) was completely deblocked by treatment with concentrated ammonium hydroxide (7 ml, 8 hours, 60° C.) and subsequent treatment in 80% acetic acid (15 minutes, ambient temperature). After evaporation of acetic acid, the solid residue was dissolved in 4% aqueous ammonium hydroxide (v/v, 4 ml) and extracted with ethyl ether (3×2 ml). The aqueous phase was concentrated to 1-2 ml and a portion applied to HPLC for purification of 12. The fractions corresponding to the major peak were pooled (ca. 2.0 O. D.$_{254}$ units) and concentrated to about 5 ml. The final product 12 was desalted on Bio-gel P-2 (1.5×100 cm) by elution with 20% aqueous ethanol, reduced to dryness and resuspended in water (200 μl) to give a solution of $A_{254}=10$. The sequence of 12 was confirmed by two-dimensional sequence analysis.

Figure 9:
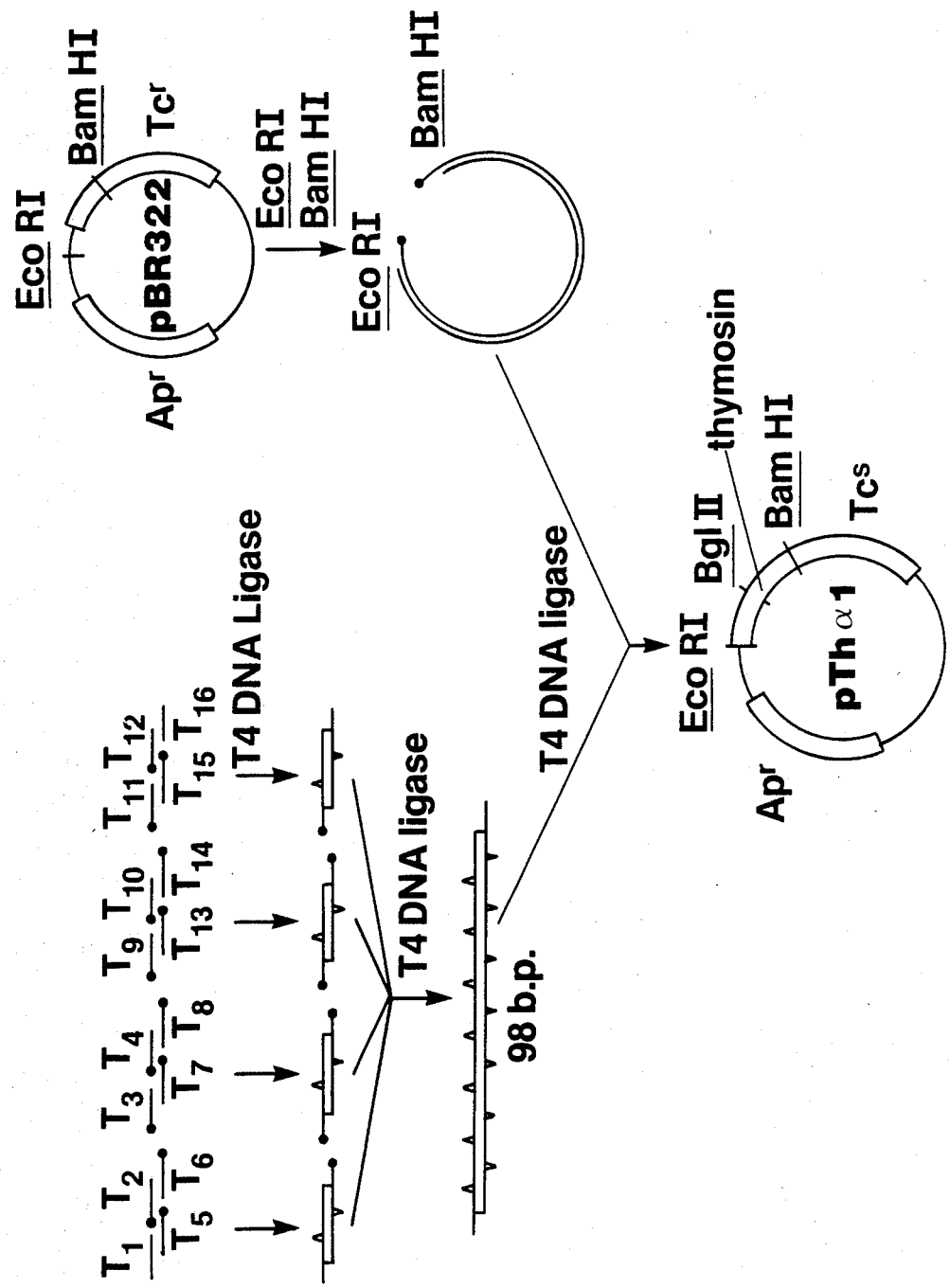

The complete thymosin alpha 1 gene was assembled from the 16 synthetic oligo-nucleotides by methods previously described in detail for somatostatin (Itakura et al., 1977), insulin (Goeddel et al., 1979), and growth hormone (Goeddel, Heyneker, et al., 1979, Nature 281:544). Ten microgram quantities of oligonucleotides $T_2$ through $T_{15}$ were quantitatively phosphorylated with [$\gamma$-$^{32}$P]-ATP (New England Nuclear) in the presence of $T_4$ polynucleotide kinase (Goeddel et al, 1979), to give specific activities of approximately 1 Ci/mmol. Radiolabelled fragments were purified by 20% polyacrylamide/7 M urea gel electrophoresis and sequences of the eluted fragments were verified by two-dimensional electrophoresis/homochromatography (Jay et al., 1974, Nucleic Acids Res. 1:331) of partial snake venom digests. Fragments $T_1$ and $T_{16}$ were left unphosphorylated to minimize undesired polymerization during subsequent ligation reactions. These oligonucleotides (2 μg each) were assembled in four groups of four fragments (see FIG. 9 of the accompanying drawings), by $T_4$ DNA ligase using published procedures (Goeddel et al., 1979). The reaction products were purified by gel electrophoresis on a 15% polyacrylamide gel containing 7 M urea (Maxam and Gilbert, 1977, Proc. Nat. Acad. Sci. USA 71:3455). The four isolated products were ligated together and the reaction mixture resolved by 10% polyacrylamide gel electrophoresis. DNA in the size range of the thymosin alpha 1 gene (90–105 base pairs) was electroeluted.

Figure 7:
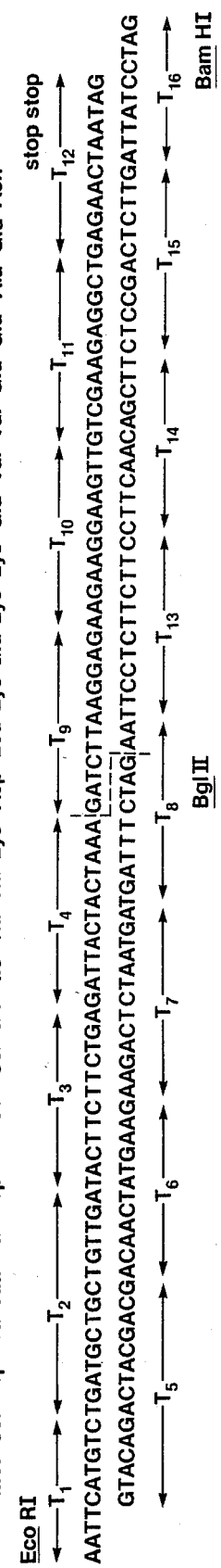

Plasmid pBR322 (0.5 μg) was treated with BamHI and EcoRI restriction endonucleases and the fragments separated by polyacrylamide gel electrophoresis. The large fragment was recovered from the gel by electroelution and subsequently ligated to the assembled synthetic DNA (Goeddel, Heyneker, et al., 1979). This mixture was used to transform *E. coli* K12 strain 294, ATCC No. 31446. Five percent of the transformation mixture was plated on LB plates containing 20 μg/ml ampicillin. The four ampicillin resistant colonies obtained were sensitive to tetracycline, suggesting insertion into the tetracycline resistance gene. Analysis of the plasmids from these four colonies showed that in each case the plasmid, designated pThα1, contained (a) a BglII site not found in pBR322 itself, thus indicating the presence of the thymosin alpha 1 gene as shown in FIG. 7, and (b) a fragment of approximately 105 base pairs generated by BamHI/EcoRI cleavage. The construction route for plasmid pThα1 (not drawn to scale), is presented in FIG. 9 of the accompanying drawings wherein the heavy dots indicate 5′-phosphate groups.

3. Reaction of Treated pThα1 and LE′(d) Fragment

The plasmid pThα1 contains a gene specifying ampicillin resistance and a structural gene specifying thymosin alpha 1 cloned at its 5′ coding strand end into an EcoRI site and at its 3′ end into a BamHI site. The thymosin gene contains a BglII site as well. To create a plasmid capable of accepting the LE′(d) fragment prepared above, pTHα1 was EcoRI digested followed by Klenow polymerase I reaction with dTTP and dATP to blunt the EcoRI residues. BglII digestion of the resulting product created a linear DNA fragment containing the gene for ampicillin resistance and, at its opposite ends, a sticky BglII residue and a blunt end. The resulting product could be recirularized by reaction with the LE′(d) fragment containing a BglII sticky end and a blunt end in the presence of $T_4$ ligase to form the plasmid pTrp24. In doing so, an EcoRI site is recreated at the position where blunt end ligation occurred.

E. Construction of Plasmid pSOM7Δ2Δ4

Successive digestion of pTrp24 with BglII and EcoRI, followed by PAGE and electroelution, yields a fragment having codons for the LE′(d) polypeptide with a BglII sticky end and an EcoRI sticky end adjacent to its 3′ coding terminus. The LE′(d) fragment can be cloned into the BglII site of plasmid pSom7Δ2 to form an LE′ polypeptide/somatostatin fusion protein expressed under the control of the tryptophan promoter/operator. To do so requires (1) partial EcoRI digestion of pSom7Δ2 in order to cleave the EcoRI site distal to the tryptophan promoter/operator, and (2) proper choice of the primer sequence in order to properly maintain the codon reading frame, and to recreate an EcoRI cleavage site.

Thus, 16 μg of plasmid pSom7Δ2 was diluted into 200 μl of buffer containing 20 mM Tris, pH 7.5, 5 mM $MgCl_2$, 0.02 NP40 detergent, and 100 mM NaCl, and treated with 0.5 units EcoRI. After 15 minutes at 37° C., the reaction mixture was phenol extracted, chloroform extracted, ethanol precipitated, and subsequently digested with BglII. The larger resulting fragment was isolated by the PAGE procedure followed by electroelution. This fragment contains the codons "LE′(p)" for the proximal end of the LE′ polypeptide, ie, those upstream from the BglII site. This fragment was next ligated to the above LE′(d) fragment in the presence of $T_4$ DNA ligase to form the plasmid pSom7Δ2Δ4, which upon transformation into *E. coli* strain 294, efficiently produced a fusin protein consisting of the fully reconstituted LE polypeptide and somatostatin under the control of the tryptophan promoter/operator.

F. Construction of Linear DNA Having a PstI Residue at the 3′ end and a BglII Residue at its 5′ End Bounding a Gene Specifying Tetracycline Resistance Plasmid pBR322 was HindIII digested and the protruding HindIII ends were digested with S1 nuclease. The S1 nuclease digestion involved treatment of 10 μg of HindIII-cleaved pBR322 in 30 μl S1 buffer (0.3M NaCl, 1 mM $ZnCl_2$, 25 mM sodium acetate, pH 4.5) with 300 units S1 nuclease for 30 minutes at 15° C. The reaction was stopped by the addition of 1 μl of 30×S1 nuclease stop solution (0.8M tris base, 50 mM EDTA). The mixture was phenol extracted, chloroform extracted, ethanol precipitated, and then EcoRI digested as previously described. The resulting fragment, obtained by the PAGE procedure followed by electroelution, has an EcoRI sticky end and a blunt end whose coding strand begins with the nucleotide thymidine. The S1-digested HindIII residue beginning with thymidine can be joined to a Klenow Polymerase I-treated BglII residue so as to reconstitute the BglII restriction site upon ligation.

Therefore plasmid pSOM7Δ2, prepared in Example 13C, was BglII digested and the resulting BglII sticky ends were made double stranded by treatment with Klenow Polymerase I using all four deoxynucleotide triphosphates. EcoRI cleavage of the resulting product, followed by PAGE and electroelution of the small fragment, yielded a linear piece of DNA containing the tryptophan promoter/operator and codons of the LE′ "proximal" sequence upstream from the BglII site ("LE'(p)"). The product had an EcoRI end and a blunt end resulting from filling in the BglII site. However, the BglII site is reconstituted by ligation of the blunt end to the blunt end of the above Sl-digested HindIII fragment. Thus, the two fragments were ligated in the presence of T4 DNA ligase to form the recircularized plasmid pHKY10 which was propagated by transformation into competent E. coli strain 294 cells. Tetracycline resistant cells bearing the recombinant plasmid pHKY10 were selected and the plasmid DNA extracted. Digestion with BglII and PstI, followed by isolation by the PAGE procedure and electroelution of the large fragment, yielded the desired linear piece of DNA having PstI and BglII sticky ends. This DNA fragment, thus produced from pHKY10, contains the origin of replication and therefore is useful as a component in the construction of plasmid pIA7Δ4Δ1 in which both the genes coding for the trp LE' polypeptide fusion protein and the tetracycline resistance are controlled by the trp promoter/operator.

G. Construction of Linear DNA Having the Trp Promoter/Operator

Plasmid pSOM7Δ2Δ4, prepared in Example 13E, was subjected to partial EcoRI digestion followed by PstI digestion. The resulting fragment contained the trp promoter/operator and was isolated by the PAGE procedure followed by electroelution. Partial EcoRI digestion was necessary to obtain a fragment which was cleaved adjacent to the 5' end of the somatostatin gene but not cleaved at the EcoRI site present between the ampicillin resistance gene and the trp promoter/operator. Ampicillin resistance lost by the PstI cut in the ampicillin resistance gene can be restored upon ligation with the final pHKY10 linear DNA derivative produced in Example 13F above.

H. Isolation of the Insulin A Chain Structural Gene

The insulin A chain structural gene was obtained by the EcoRI and BamHI digestion of plasmid pIAl, whose construction is disclosed in Goeddel et al., 1979, Proc. Nat. Acad. Sci. USA 76:106. The desired fragment was purified by PAGE and electroelution and had EcoRI and BamHI termini.

Figure 3:
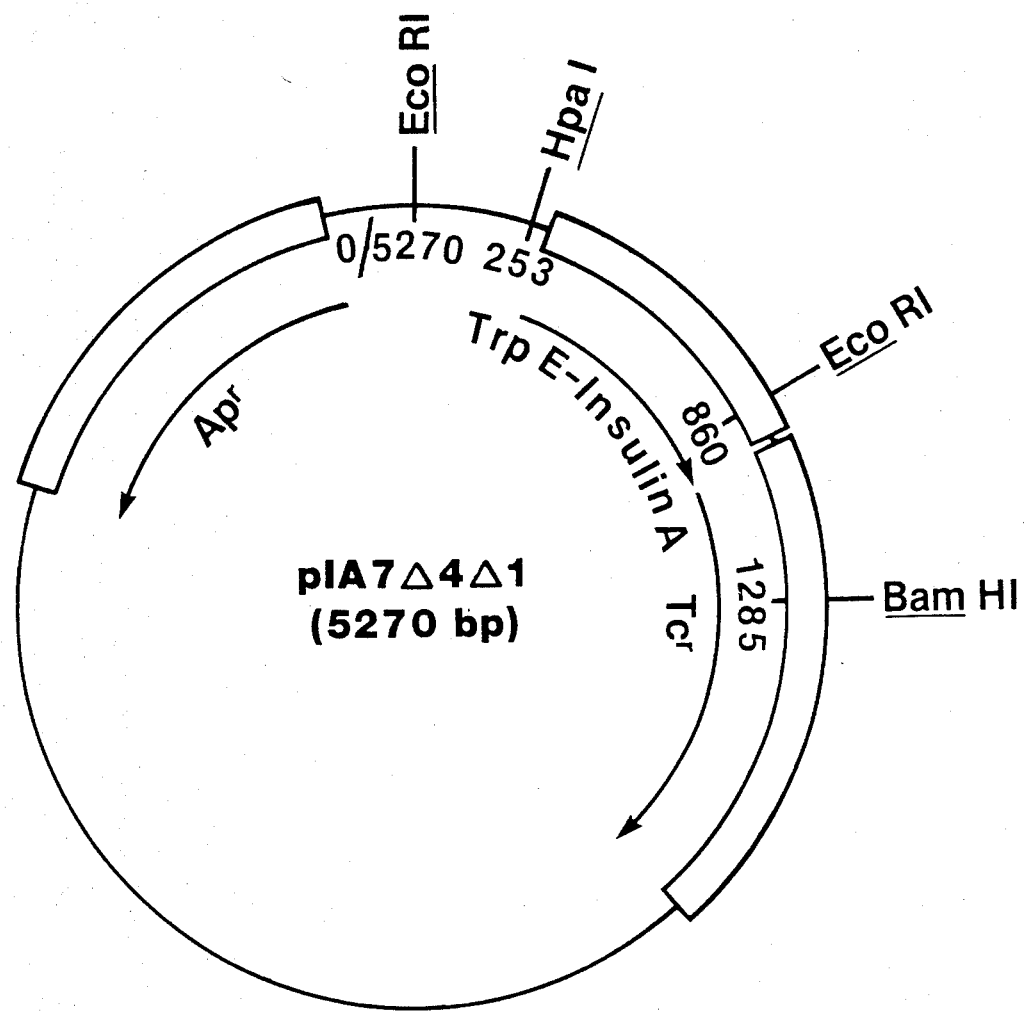

I. Ligation of the Insulin A Chain Structural Gene, the Trp Promoter/Operator, and the pHKY10 Linear DNA Fragment Having PstI and BglII Termini The Insulin A Chain structural gene, the linear DNA fragment containing the trp promoter/operator (prepared in Example 13G), and the pHKY10 linear DNA fragment (prepared in Example 13F), were ligated together in proper orientation, as depicted in FIG. 3, to form the desired plasmid pIA7Δ4Δ1. Plasmid pIA7Δ4Δ1 can be readily selected because of the restoration of ampicillin and tetracycline resistance.

EXAMPLE 14

Construction of Recombinant Plasmid pPR1

Plasmid pIA7Δ4Δ1 contains a single BamHI restriction site that allows for the insertion of the λcI and λrex containing 2.5 Kb BglII fragment of bacteriophage lambda. This was done in substantial accordance with the teaching of Example 1. Thus the desired pPR1 plasmid was produced by the ligation of the λBglII fragment into the BamHI site of pIA7Δ4Δ1.

EXAMPLE 15

Transformation of Recombinant Plasmid pPR1 Into E. coli K12 C600R$_k$-M$_k$

The desired transformation was carried out in substantial accordance with the teaching of Example 2, except that the E. coli cells were transformed with DNA prepared in Example 14 rather than Example 1. Transformants were designated E. coli K12 C600R$_k$-M$_k$-/pPR1 and were selected and cultured. The resultant colonies were tested for the expected phenotypes and were used for isolation and amplification of the plasmid pPR1. Restriction enzyme analysis of plasmid pPR1 showed that the λrex, rather than the λcI, gene was closest to the trp E-insulin A chain gene. Plasmids with the reverse orientation were not found among the above produced transformants.

EXAMPLE 16

Amplification, Isolation, and Subsequent Transformation of Plasmid pPR1 Into E. coli K12 RV308

The amplification and isolation of the plasmid DNA of E. coli K12 C600R$_k$-M$_k$-/pPR1 was carried out in substantial accordance with the teaching of Example 3. The subsequent transformation of plasmid pPR1 into E. coli K12 RV308 is carried out in substantial accordance with the teaching of Example 4 to produce the desired E. coli K12 RV308/pPR1 transformants.

EXAMPLE 17

Construction of E. coli K12 RV308λcI90/pPR1 by Lysogenization with λcI90

The desired construction is carried out in substantial accordance with the teaching of Example 5. The resulting E. coli K12 RV308λcI90/pPR1 colonies can be tested to verify growth at 32° C. and sensitivity at 42° C.

EXAMPLE 18

Transformation of Recombinant Plasmid pPR1 Into E. coli K12 C600

The desired construction is carried out in substantial accordance with the teaching of Example 4. Surviving colonies can be tested for the expected phenotypes and constitute the desired E. coli K12 C600/pPR1 transformants.

EXAMPLE 19

Construction of E. coli K12 C600λcI90/pPR1 by Lysogenization with λcI90

The desired construction is carried out in substantial accordance with the teaching of Example 5. The resulting E. coli K12 C600λcI90/pPR1 colonies can be tested to verify growth at 32° C. and sensitivity at 42° C.

EXAMPLE 20

Construction of E. coli K12 C600R$_k$-M$_k$-λcI90/pPR1 by Lysogenization with λcI90

The desired construction was obtained by preparing E. coli K12 C600R$_k$-M$_k$-/pPR1, as described in Example 14, and then lysogenizing the transformants with bacteriophage λcI90 in substantial accordance with the teaching of Example 5. Surviving colonies were tested for the expected phenotypes and constituted the desired strain.

EXAMPLE 21

Construction of Plasmid pIB7Δ4Δ1

The desired plasmid was constructed in accordance with Example 13A-I except that the structural gene specifying the insulin B chain, rather than the insulin A chain, was used in the final ligation. The insulin B chain structural gene was obtained by the EcoRI and BamHI digestion of plasmid pIBl, whose construction is disclosed in Goeddel et. al., 1979. The insulin B chain encoding DNA fragment was purified by PAGE and electroelution and had EcoRI and BamHI termini.

Figure 5:
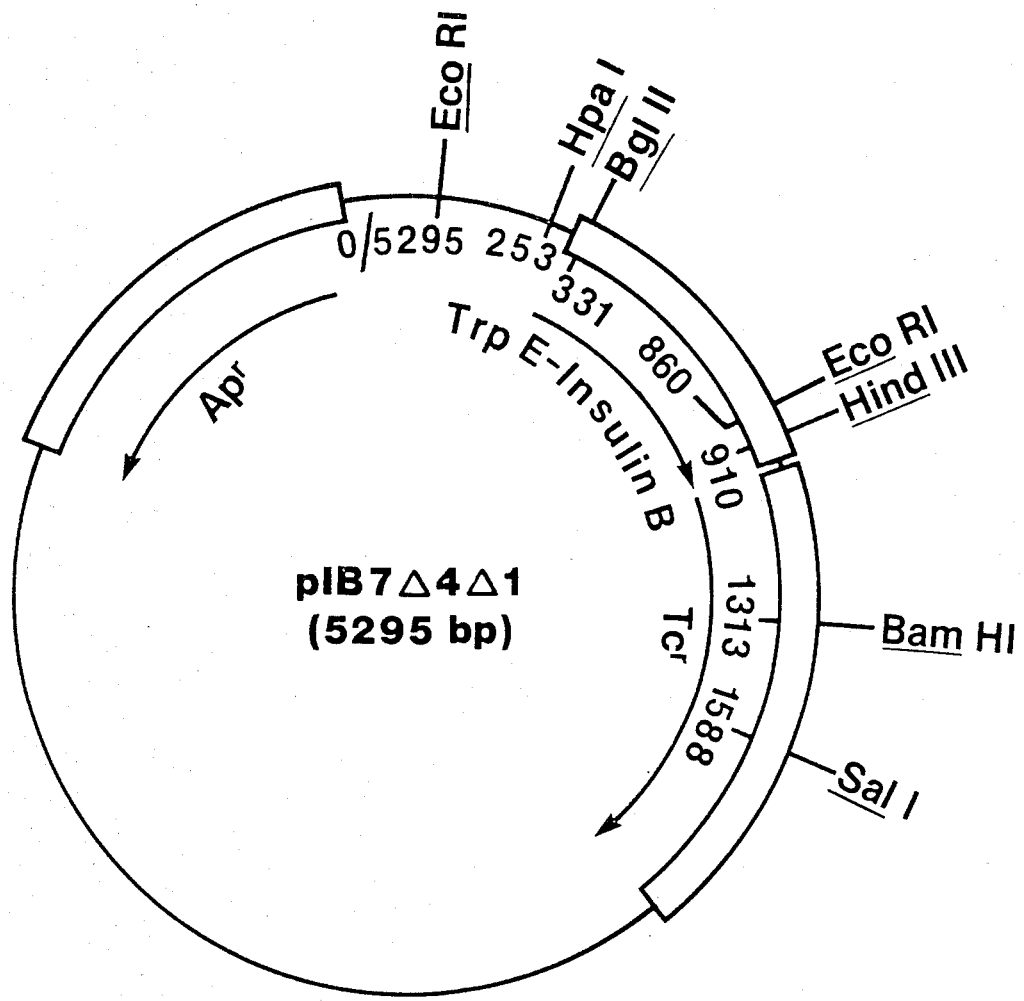

Plasmid pIB7Δ4Δ1 is depicted in FIG. 5 and can be readily selected because of the restoration of ampicillin and tetracycline resistance.

EXAMPLE 22

Construction of Recombinant Plasmid pPR3

The unique BamHI restriction site in plasmid pIB7Δ4Δ1 allows for the cloning of the λcI and λrex gene containing 2.5 Kb BglII fragment of bacteriophage lambda onto pIB7Δ4Δ1. This can be done in substantial accordance with the teaching of Example 1. Thus, ligation of the λBglII fragment into the BamHI site of pIA7Δ4Δ1 produces the desired plasmid pPR3.

EXAMPLE 23

Transformation of Recombinant Plasmid pPR3 Into E. coli K12 C600R$_k$-M$_k$

Transformation was carried out in substantial accordance with the teaching of Example 2, except that the E. coli cells were transformed with DNA prepared in Example 22 rather than Example 1.

Transformants were designated E. coli K12 C600R$_k$-M$_k$-/pPR3 and were selected and cultured. The resultant colonies were tested for the expected phenotypes and used for isolation and amplification of the plasmid pPR3. Restriction enzyme analysis of plasmid pPR3 showed that the λrex, rather than the λcI, gene was closest to the trp E-insulin B chain gene. Plasmids with the reverse orientation were not found among the above produced transformants.

EXAMPLE 24

Amplification, Isolation, and Subsequent Transformation of Recombinant Plasmid pPR3 Into E. coli K12 RV308

The plasmid DNA of E. coli K12 C600R$_k$-M$_k$-/pPR3 was amplified and isolated in substantial accordance with the teaching of Example 3. The subsequent transformation of plasmid pPR3 into E. coli K12 RV308 to produce E. coli K12 RV308/pPR3 is done in substantial accordance with the teaching of Example 4.

EXAMPLE 25

Transformation of Recombinant Plasmid pPR3 Into E. coli K12 C600

The transformation of pPR3 into E. coli K12 C600 to produce E. coli K12 C600/pPR3 is done in substantial accordance with the teaching of Example 4. Surviving colonies can be tested for the expected phenotypes and constitute the desired E. coli K12 C600/pPR3 transformants.

EXAMPLE 26

Construction of E. coli K12 RV308λcI90/pPR3 by Lysogenization with λcI90

The desired construction is made by lysogenizing E. coli K12 RV308/pPR3 with bacteriophage λcI90 in substantial accordance with the teaching of Example 5. The resulting E. coli K12 RV308λcI90/pPR3 colonies can be tested to verify growth at 32° C. and sensitivity at 42° C.

EXAMPLE 27

Construction of E. coli K12 C600λcI90/pPR3 by Lysogenization with λcI90

The desired construction is made by lysogenizing E. coli K12 C600/pPR3 with bacteriophage λcI90 in substantial accordance with the teaching of Example 5. The resulting E. coli K12 C600λcI90/pPR3 colonies can be tested to verify growth at 32° C. and sensitivity at 42° C.

EXAMPLE 28

Construction of E. coli K12 C600R$_k$-M$_k$-λcI90/pPR3 by Lysogenization with λcI90

The desired construction was obtained by preparing E. coli K12 C600R$_k$-M$_k$-/pPR3, as described in Example 21, and then lysogenizing the transformants with bacteriophage λcI90 in substantial accordance with the teaching of Example 5. The resulting E. coli K12 C600R$_k$-M$_k$-λcI90/pPR3 colonies were tested to verify growth at 32° C. and sensitivity at 42° C.

EXAMPLE 29

Method For Determining Stabilities of Host Cells Containing Recombinant Plasmid pPR3 With and Without Selection Strains to be tested for plasmid retention were maintained in logrithmic growth in non-selective media (L-broth) by periodic subculturing into fresh media The degree of plasmid retention was determined by the method of Example 12.

Other representative strains which are constructed in accordance with the foregoing teaching include:

| Example No. | Name |
| --- | --- |
| 30 | E. coli K12 RV308λcI857/pAR1 |
| 31 | E. coli K12 C600λcI90/pAR1 |
| 32 | E. coli K12 C600R$_k$-M$_k$-λcI90/pAR1 |
| 33 | E. coli K12 C600/pAR1 |
| 34 | E. coli K12 C600/pAR2 |

Stabilities of recombinant plasmids were measured as described above in Examples 12 and 29. The results are presented as percentages in Table 2, for strains E. coli K12 RV308λcI90/pAR2 and E. coli K12 RV308/pIA2, and in Table 3, for strains E. coli K12 C600R$_k$-M$_k$-λcI90/pPR3 and E. coli K12 C600R$_k$-M$_k$-/pPR3.

TABLE 2

| | Stabilities of Recombinant Plasmids | |
| --- | --- | --- |
| Number of | Percentage of Plasmid Retention | |
| Culture Doublings | E. coli K12 RV308λcI90/pAR2 | E. coli K12 RV308/pIA2 |
| 9 | 100 | 100 |
| 14 | 100 | 36 |
| 23 | 100 | 22 |

TABLE 2-continued

| Number of Culture Doublings | Stabilities of Recombinant Plasmids Percentage of Plasmid Retention | |
|---|---|---|
| | E. coli K12 RV308λcI90/pAR2 | E. coli K12 RV308/pIA2 |
| 32 | 83 | 13 |
| 40 | 82 | 9 |

TABLE 3

| Number of Culture Doublings | Stabilities of Recombinant Plasmids Percentage of Plasmid Retention | |
|---|---|---|
| | E. coli K12 C600R$_k$-M$_k$-λcI90/pPR3 | E. coli K12 C600R$_k$-M$_k$-/pPR3 |
| 0 | 100 | 100 |
| 34 | 100 | 0 |

Results in Tables 2 and 3 clearly demonstrate the superiority of the selective system for maintaining recombinant plasmids in bacterial populations. About 78 percent of the cells in the culture of E. coli K12 RV308/pIA2 were plasmid minus after 23 culture doublings and about 100 percent of the cells in the culture E. coli K12 C600R$_k$-M$_k$-/pPR3 were plasmid minus after 34 culture doublings. Moreover, after 23 and 34 culture doublings respectively, none of the cells in the culture of E. coli K12 RV308λcI90/pAR2 and E. coli C600 R$_k$-M$_k$λcI90/pPR3 that had the selective system in place, were plasmid minus. After more extensive growth some minor plasmid segregation was seen. However the results probably reflect recombination between the prophage and plasmid.

Plasmid stability in constructed strain E. coli K12 C600R$_k$-M$_k$-λcI857/pAR1 was determined by culturing the strain in L-broth overnight separately at 42° C. (restrictive conditions) and 32° C. (permissive conditions). The frequency of plasmid+ cells was taken as the ratio of colonies at 42° C. to the total number of colonies that grew at 32° C. The ratio was expressed as a percentage. Results indicate that about 46 percent of the cells in the culture grown under permissive conditions and therefore without the present invention were plasmid minus, while none of the cells in the culture grown under restrictive conditions and consequently with the invention were plasmid minus at that culture stage. Clearly the present invention is quite useful and effective for maintaining recombinant plasmids in bacterial populations.

We claim:

1. A method for stabilizing and selecting bacterial host cells containing recombinant DNA which expresses a functional polypeptide comprising:
   (a) transforming the bacterial host cells with a recominant DNA cloning vector which contains both a repressor gene and a gene which expresses a functional polypeptide; and
   (b) lysogenizing the transformed bacterial host cells with a bacteriophage lysogenic organism containing a marker which is lethal in the bacterial host cells but which is repressed in the transformed bacterial host cells by the repressor gene contained in the recombinant DNA cloning vector;
subject to the limitation that the recombinant DNA cloning vector contains a replicon and a promoter which are not sensitive to the repressor, and subject to the further limitation, that when the bacterial host cells are lysogenized with a bacteriophage lysogenic organism containing a gene which is conditionally lethal, the resulting bacterial host cells are cultured under restrictive conditions.

2. The method of claim 1 in which the recombinant DNA cloning vector is a plasmid.

3. The method of claim 1 which the recombinant DNA cloning vector is a bacteriophage.

4. The method of Claim 1 in which the gene which expresses a functional polypeptide is selected from the group consisting of genes coding for human insulin, human pre-proinsulin, human proinsulin, human insulin A-chain, human insulin B-chain, non-human insulin, human growth hormone, non-human growth hormone, human interferon, non-human interferon, viral antigen, urokinase, any polypeptide, any peptide hormone, and any peptide enzyme.

5. The method of Claim 1 in which the repressor gene is selected from the group consisting of chromosomal DNA replication mutation repressors, cell wall synthesis mutation repressors, ribosome mutation repressors, RNA polymerase mutation repressors, tRNA mutation repressors, amino acyl tRNA synthetase mutation repressors, cell division mutation repressors, and nonsense mutation repressors.

6. The method of Claim 1 in which the repressor gene is a cI repressor gene of bacteriophage lambda.

7. The method of Claim, 6 in which the cI repressor gene is cI857.

8. The method of Claim 1 in which the repressor gene is the λcro gene of bacteriophage lambda.

9. The method of Claim 1 in which the repressor gene is temperature sensitive and is inactivated at or above a temperature within a certain temperature range.

10. The method of Claim 9 in which the temperature range is 38° C. to 44° C.

11. The method of Claim 1 in which the lysogenic organism contains a bacteriophage λcI gene which does not produce a functional cI repressor.

12. The method of Claim 11 in which the lysogenic organism is bacteriophage lambda cI90.

13. The method of Claim 1 in which the lysogenic organism is bacteriophage λcI857.

14. The method of Claim 1 in which the bacteria are selected from the group consisting of E. coli, E. coli K12, E. coli K12 RV308, E. coli K12 C600R$_k$-M$_k$-, Bacillus, Bacillus subtilis, Staphylococcus, Streptococcus, Actinomycetes, Streptomyces, Serratia, Pseudomonas, and Agrobacterium.

15. The method of Claim 14 in which the bacteria are E. coli.

16. The method of Claim 14 in which the bacteria are E. coli K12.

17. The method of Claim 14 in which the bacteria are E. coli K12 RV308.

18. The method of Claim 14 in which the bacteria are E. coli K12 C600R$_k$-M$_k$-.

19. The method of claim 14 in which the bacteria are Streptomyces.

20. The method of claim 1 in which the recombinant DNA cloning vector is plasmid pAR2.

21. The method of claim 1 in which the recombinant DNA cloning vector is pAR1.

22. The method of claim 1 in which the transformed host cells are E. coli K12 RV308/pAR2.

23. The method of claim 1 in which the transformed host cells are E. coli K12 RV308/pAR1.

24. The method of claim 1 in which the tansformed host cells are E. coli K12 C600R$_k$-M$_k$-/pAR1.

25. The method of Claim 1 in which the lysogenized transformed host cells are *E. coli* K12 RV308λcI90-/pAR2.

26. The method of Claim 1 in which the lysogenized transformed host cells are *E. coli* K12 RV308λcI90-/pAR1.

27. The method of Claim 1 in which the lysogenized transformed host cells are *E. coli* K12 C600R$_k$-M$_k$-λcI857/pAR1.

28. A transformed bacterial host cell comprising:
(a) a recombinant DNA cloning vector containing both a repressor gene and a gene which expresses a functional polypeptide; and
(b) a chromosomal marker which is lethal or conditionally lethal but which is repressed by the repressor gene contained in the recombinant DNA cloning vector;
subject to the limitation that the recombinant DNA cloning vector contains a replicon and a promoter which are not sensitive to the repressor.

29. The transformed host cell of Claim 28 in which the recombinant DNA cloning vector is a plasmid.

30. The transformed host cell of Claim 28 in which the recombinant DNA cloning vector is a bacteriophage.

31. The transformed host cell of claim 28 in which the gene which expresses a functional polypeptide is selected from the group of genes consisting of naturally occurring genes, non-naturally occurring genes, and genes which are in part naturally occurring and are in part synthetic or non-naturally occurring.

32. The transformed host cell of claim 28 in which the gene which expresses a functional polypeptide is selected from the group consisting of genes coding for human insulin, human pre-proinsulin, human proinsulin, human insulin A-chain, human insulin B-chain, non-human insulin, human growth hormone, non-human growth hormone, human interferon, non-human interferon, viral antigen, urokinase, any polypeptide, any peptide hormone, and any peptide enzyme.

33. The transformed host cell of claim 28 in which the repressor gene is selected from the group consisting of chromosomal DNA replication mutation repressors, cell wall synthesis mutation repressors, ribosome mutation repressors, RNA polymerase mutation repressors, tRNA mutation repressors, DNA restriction and modification mutation repressors, amino acyl tRNA synthetase mutation repressors, cell division mutation repressors, and nonsense mutation repressors.

34. The transformed host cell of claim 28 in which the repressor gene is a cI repressor gene of bacteriophage lambda.

35. The transformed host cell of claim 34 in which the repressor gene is cI857.

36. The transformed host cell of claim 28 in which the repressor gene is temperature sensitive and is inactivated at or above a temperature within a certain temperature range.

37. The transformed host cell of claim 36 in which the temperature range is 38° C. to 44° C.

38. The transformed host cell of Claim 28 in which the chromosomal marker is a bacteriophage λcI gene which does not produce a functional cI repressor.

39. The transformed host cell of Claim 38 in which the λcI gene is bacteriophage lambda cI90.

40. The transformed host cell of Claim 28 in which the chromosomal marker is bacteriophage λcI857.

41. The bacterium of Claim 38 which is selected from the group consisting of *E. coli, E. coli* K12, *E. coli* K12 RV308, *E. coli* K12 C600R$_k$-M$_k$-, Bacillus, *Bacillus subtilis,* Staphylococcus, Streptococcus, Actinomycetes, Streptomyces, Serratia, Pseudomonas, and Agrobacterium.

42. The bacterium of claim 41 which is *E. coli.*

43. The bacterium of claim 41 which is *E. coli* K12.

44. The bacterium of claim 41 which is *E. coli* K12 RV308.

45. The bacterium of claim 41 which is *E. coli* K12 C600R$_k$-M$_k$-.

46. The bacterium of claim 41 which is Streptomyces.

47. *E. coli* K12 Rv308λcI90/pAR2.

48. *E. coli* K12 RV308/pAR2.

49. *E. coli* K12 RV308λcI90/pAR1.

50. *E. coli* K12 RV308/pAR1.

51. *E. coli* K12 C600R$_k$-M$_k$-/pAR1.

52. *E. coli* K12 C600R$_k$-M$_k$-λcI857/pAR1.

53. *E. coli* K12 C600R$_k$-M$_k$-λcI90/pAR2.

54. Plasmid pAR2.

55. Plasmid pAR1.

56. A method for lysing recombinant DNA containing bacterial host cells comprising:
(a) the method of claim 10 in which the repressor gene represses a marker that causes host cell lysis; and
(b) culturing the bacterial host cells at a temperature which inactivates the repressor and, in the case of a conditional lethal marker, at a temperature which is not within the temperature range for permissive culture of the host cells.

57. The method of claim 56 in which the temperature which inactivates the repressor is from 38° to 44° C.

58. The method of claim 56 in which the recombinant DNA cloning vector is a plasmid.

59. The method of claim 56 in which the recombinant DNA cloning vector is a bacteriophage.

60. The method of claim 56 in which the genes which express a functional polypeptide are selected from the group consisting of genes coding for human insulin, human pre-proinsulin, human proinsulin, human insulin A-chain, human insulin B-chain, non-human insulin, human growth hormone, non-human growth hormone, human interferon, non-human interferon, viral antigen, urokinase, any polpeptide, any peptide hormone, and any peptide enzyme.

61. The method of claim 56 in which the repressor gene is selected from the group consisting of chromosomal DNA replication mutation repressors, cell wall synthesis mutation repressors, ribosome mutation repressors, RNA polymerase mutation repressors, tRNA mutation repressors, amino acyl tRNA synthetase mutation repressors, cell division mutation repressors, and nonsense mutation repressors.

62. The method of claim 56 in which the repressor gene is a cI repressor gene of bacteriophage lambda.

63. The method of claim 62 in which the cI repressor gene is cI857.

64. The method of claim 56 in which the lysogenic organism contains a bacteriophage λcI gene which does not produce a functional cI repressor.

65. The method of claim 64 in which the lysogenic organism is bacteriophage lambda cI90.

66. The method of claim 56 in which the bacteria are selected from the group consisting of *E. coli, E. coli* K12, *E. coli* K12 RV308, *E. coli* K12 C600R$_k$-M$_k$-, Bacillus, *Bacillus subtilis,* Staphylococcus, Streptococcus, Actinomycetes, Streptomyces, Serratia, Pseudomonas, and Agrobacterium.

67. The method of claim 66 in which the bacteria are *E. coli.*

68. The method of claim 66 in which the bacteria are *E. coli* K12.

69. The method of claim 66 in which the bacteria are *E. coli* K12 RV308.

70. The method of claim 66 in which the bacteria are *E. coli* K12 C600$R_k$-$M_k$-.

71. The method of claim 66 in which the bacteria are Streptomyces.

72. The method of claim 56 in which recombinant DNA cloning vector is plasmid pAR2.

73. The method of claim 56 in which the transformed host cells are *E. coli* K12 RV308/pAR2.

74. The method of claim 56 in which the transformed host cells are *E. coli* K12 C600/pAR2.

75. The method of claim 56 in which the transformed host cells are *E. coli* K12 C600$R_k$-$M_k$-/pAR2.

76. The method of claim 56 in which the lysogenized transformed host cells are *E. coli* K12 RV308λcI90-/pAR2.

77. The method of claim 56 in which the lysogenized transformed host cells are *E. coli* K12 C600$R_k$-$M_k$-λI90-/pAR2.

78. The method of claim 56 in which the lysogenized transformed host cells are *E. coli* K12 C600λcI90-/pAR2.

79. A method for lysing recombinant DNA containing bacterial host cells which comprises lysogenizing the bacterial host cells with a bacteriophage lysogenic organism containing a conditional lethal marker which causes host cell lysis and culturing the lysogenized bacterial host cells under restrictive conditions.

80. A method for lysing bacterial host cells which comprises transforming the bacterial host cells with a recombinant DNA cloning vector which contains a conditional lethal marker which causes host cell lysis and culturing the transformed bacterial host cells under restrictive conditions.

81. The method of claim 79 or 80 wherein the conditional lethal marker is bacteriophage λcI857.

82. The method of claim 1 in which the recombinant DNA cloning vector is plasmid pPR1.

83. The method of claim 1 in which the recombinant DNA cloning vector is plasmid pPR3.

84. The method of claim 1 in which the transformed host cells are *E. coli* K12 RV308/pPR1.

85. The method of claim 1 in which the transformed host cells are *E. coli* K12 RV308/pPR3.

86. The method of claim 1 in which the transformed host cells are *E. coli* K12 C600/pPR1.

87. The method of claim 1 in which the transformed host cells are *E. coli* K12 C600/pPR3.

88. The method of claim 1 in which the transformed host cells are *E. coli* K12 C600$R_k$-$M_k$-/pPR1.

89. The method of claim 1 in which the transformed host cells are *E. coli* K12 C600$R_k$-$M_k$-/pPR3.

90. The method of claim 1 in which the transformed host cells are *E. coli* K12 C600/pAR1.

91. The method of claim 1 in which the transformed host cells are *E. coli* K12 C600/pAR2.

92. The method of claim 1 in which the transformed host cells are *E. coli* K12 C600$R_k$-$M_k$-/pAR2.

93. The method of claim 1 in which the lysogenized transformed host cells are *E. coli* K12 RV308λcI90/pPR1.

94. The method of claim 1 in which the lysogenized transformed host cells are *E. coli* K12 RV308λcI90/pPR3.

95. The method of claim 1 in which the lysogenized transformed host cells are *E. coli* K12 C600λcI90/pPR1.

96. The method of claim 1 in which the lysogenized transformed host cells are *E. coli* K12 C600λcI90/pPR3.

97. The method of claim 1 in which the lysogenized transformed host cells are *E. coli* K12 C600$R_k$-$M_k$-λcI90/pPR1.

98. The method of claim 1 in which the lysogenized transformed host cells are *E. coli* K12 C600$R_k$-$M_k$-λcI90/pPR3.

99. The method of claim 1 in which the lysogenized transformed host cells are *E. coli* K12 C600λcI857-/pAR1.

100. The method of claim 1 in which the lysogenized transformed host cells are *E. coli* K12 C600λcI90-/pAR2.

101. The method of claim 1 in which the lysogenized transformed host cells are *E. coli* K12 RV308λcI857-/pAR1.

102. The method of claim 1 in which the lysogenized transformed host cells are *E. coli* K12 C600λcI90-/pAR1.

103. The method of claim 1 in which the lysogenized transformed host cells are *E. coli* K12 C600$R_k$-$M_k$-λcI90/pAR1.

104. The method of claim 1 in which the host cells are *E. coli* K12 C600.

105. The bacterium of claim 28 which is *E. coli* K12 C600.

106. An organism selected from the group consisting of *E. coli* K12 RV308/pPR1, *E. coli* K12 RV308/pPR3, *E. coli* K12 C600/pPR1, *E. coli* K12 C600/pPR3, *E. coli* K12 C600$R_k$-$M_k$-/pPR1, *E. coli* K12 C600$R_k$-$M_k$-/pPR3, *E. coli* K12 C600/pAR1, *E. coli* K12 C600/pAR2, *E. coli* K12 C600$R_k$-$M_k$-/pAR2, *E. coli* K12 RV308λcI90/pPR1, *E. coli* K12 RV308λcI90/pPR3, *E. coli* K12 C600λcI90/pPR1, *E. coli* K12 C600λcI90/pPR3, *E. coli* K12 C600$R_k$-$M_k$-λcI90/pPR1, *E. coli* K12 C600$R_k$-$M_k$-λcI90/pPR3, *E. coli* K12 C600λcI857/pAR1, *E. coli* K12 C600λcI90-/pAR2, *E. coli* K12 RV308λcI857/pAR1, *E. coli* K12 C600λcI90/pAR1, and *E. coli* K12 C600$R_k$-$M_k$-λcI90-/pAR1.

107. The organism of claim 106 which is *E. coli* K12 RV308/pPR1.

108. The organism of claim 106 which is *E. coli* K12 RV308/pPR3.

109. The organism of claim 106 which is *E. coli* K12 C600/pPR1.

110. The organism of claim 106 which is *E. coli* K12 C600/pPR3.

111. The organism of claim 106 which is *E. coli* K12 C600$R_k$-$M_k$-/pPR1.

112. The organism of claim 106 which is *E. coli* K12 C600$R_k$-$M_k$-/pPR3.

113. The organism of claim 106 which is *E. coli* K12 C600/pAR1.

114. The organism of claim 106 which is *E. coli* K12 C600/pAR2.

115. The organism of claim 106 which is *E. coli* K12 C600$R_k$-$M_k$-/pAR2.

116. The organism of claim 106 which is *E. coli* K12 RV308λcI90/pPR1.

117. The organism of claim 106 which is *E. coli* K12 RV308λcI90/pPR3.

118. The organism of claim 106 which is *E. coli* K12 C600λcI90/pPR1.

119. The organism of claim 106 which is *E. coli* K12 C600λcI90/pPR3.

120. The organism of claim 106 which is *E. coli* K12 C600R$_k$-M$_k$-λcI90/pPR1.

121. The organism of claim 106 which is *E. coli* K12 C600R$_k$-M$_k$-λcI90/pPR3.

122. The organism of claim 106 which is *E. coli* K12 C600λcI857/pAR1.

123. The organism of claim 106 which is *E. coli* K12 C600λcI90/pAR2.

124. The organism of claim 106 which is *E. coli* K12 RV308λcI857/pAR1.

125. The organism of claim 106 which is *E. coli* K12 C600λcI90/pAR1.

126. The organism of claim 106 which is *E. coli* K12 C600R$_k$-M$_k$-λcI90/pAR1.

127. Plasmid pPR1.

128. Plasmid pPR3.

129. The method of claim 56 in which the recombinant DNA cloning vector is plasmid pPR1.

130. The method of claim 56 in which the recombinant DNA cloning vector is plasmid pPR3.

131. The method of claim 56 in which the lysogenized transformed host cells are *E. coli* K12 RV308λcI90/pPR1.

132. The method of claim 56 in which the lysogenized transformed host cells are *E. coli* K12 RV308λcI90/pPR3.

133. The method of claim 56 in which the lysogenized transformed host cells are *E. coli* K12 C600λcI90/pPR1.

134. The method of claim 56 in which the lysogenized transformed host cells are *E. coli* K12 C600R$_k$-M$_k$-λcI90/pPR3.

* * * * *